US006740486B1

(12) United States Patent
Lai et al.

(10) Patent No.: US 6,740,486 B1
(45) Date of Patent: May 25, 2004

(54) NUCLEIC ACID AND POLYPEPTIDE P10 OF A BORNA DISEASE VIRUS (BDV) AND THEIR USE FOR DIAGNOSTIC AND IMMUNIZATION PURPOSES

(75) Inventors: Patrick K. Lai, Bridgeport, WV (US); Tahir H. Malik, Salem, WV (US)

(73) Assignee: Salem International University (Salem-Teikyo University), Salem, WV (US)

( * ) Notice: Subject to any disclaimer, the term of this patent is extended or adjusted under 35 U.S.C. 154(b) by 0 days.

(21) Appl. No.: 09/763,509

(22) PCT Filed: Aug. 24, 1999

(86) PCT No.: PCT/US99/19227

§ 371 (c)(1), (2), (4) Date: Feb. 23, 2001

(87) PCT Pub. No.: WO00/12548

PCT Pub. Date: Mar. 9, 2000

Related U.S. Application Data

(60) Provisional application No. 60/097,901, filed on Aug. 26, 1998.

(51) Int. Cl.[7] .............................. C12Q 1/70; C12Q 1/68; C07K 14/08; C07H 21/00
(52) U.S. Cl. .............................. 435/5; 435/6; 435/320.1; 530/324; 530/350; 536/23.4; 536/23.72
(58) Field of Search .................................. 530/324, 350; 424/186.1, 204.1; 435/5, 69.3, 69.7, 6; 536/23.72, 23.4

(56) References Cited

FOREIGN PATENT DOCUMENTS

CA 2197847 A1 * 8/1997

* cited by examiner

*Primary Examiner*—Donna C. Wortman
(74) *Attorney, Agent, or Firm*—Steptoe & Johnson PLLC

(57) ABSTRACT

One aspect of the present invention is a polypeptide having at least one bioactivity of a polypeptide p10 of a Borna Disease Virus. A second aspect of the present invention is a specific binding member, such as an antibody, that binds with at least a portion of a polypeptide p10 of a Borna Disease Virus. A third aspect of the present invention is a nucleic acid molecule that encodes a polypeptide having at least one bioactivity of a polypeptide p10 of a Borna Disease Virus. A fourth aspect of the present invention is a test kit that includes at least one of: a polypeptide of the present invention, a specific binding member of the present invention or a nucleic acid molecule of the present invention. A fifth aspect of the present invention is a vaccine and method of immunization that includes at least one of: a polypeptide of the present invention, a specific binding member of the present invention or a nucleic acid molecule of the present invention. A sixth aspect of the present invention is a method of diagnosis that includes at least one of: a polypeptide of the present invention, a specific binding member of the present invention or a nucleic acid molecule of the present invention. A seventh aspect of the present invention is a method of identifying a test compound or bioactivity, preferably bioactivities that are useful in the present invention.

11 Claims, 9 Drawing Sheets

FIG. 2

ATGGGTTCCGACCTCCGGCTGACATTGCTTGAACTAGTCAGGAGGCTCAA
TGGCAACGCGACCATCGAGTCTGGTCGACTCCCTGGAGGACGAAGAAGA
TCCCCAGACACTACGACGGGAACGATCGGGGTCACCAAGACCACGGAAG
ATCCCAAGGAATGCATTGACCCAACCAGTCGACCAGCTCCTGAAGGACCT
CAGGAAGAACCCCTCCATGATCTCAGACCCAGACCAGCGAACCGGAAGG
GAGCAGCTATCGAAGACTACAAGGACGACGATGACAAG

FIG. 3

MGSDLRLTLLELVRRLNGNATIESGRLPGGRRRSPDTTTGTIG
VTKTTEDPKECIDPTSRPAPEGPQEEPLHDLRPRPANRKGAAIE
DYKDDDDK

NUCLEIC ACID AND POLYPEPTIDE P10 OF A BORNA DISEASE VIRUS (BDV) AND THEIR USE FOR DIAGNOSTIC AND IMMUNIZATION PURPOSES

RELATED APPLICATIONS

This application claims the benefit of U.S. provisional patent application No. 60/097,901 filed Aug. 26, 1998, which is incorporated herein by reference in its entirety.

GOVERNMENT SUPPORT

This invention was made partially with government support awarded by the National Institute of Mental Health, the National Institutes of Health, the Public Health Service (Grant No. MH57740). The United States Government may have certain rights in the invention.

TECHNICAL FILED

The present invention is directed to the 10 kilodalton polypeptide p10 of a Borna Disease Virus (BDV) and its coding nucleic acid sequence. Both can be used in the detection of, and the vaccination against, a BDV and related infections and diseases.

BACKGROUND

The Borna Disease virus (BDV) is an enveloped, negative sense, nonsegmented, single-stranded RNA virus which causes Borna Disease (BD), a transmissible polioencephalomyelitis, in susceptible animals. The Borna Disease was originally described in horses and sheep, but cattle, rabbits, goats, deer, llamas, alpacas, cats and ostriches can also be naturally infected. Recent reports indicate that the BDV also can infect humans. The virus can be isolated from the naturally infected hosts. The isolates from different species exhibit high degrees of homology, but it is not clear whether they are the same virus originally described as the causative agent of BD in horses or they are closely related viruses. However, viral proteins from one isolate can react with BDV-specific antibodies in the serum of another species, and vice versa.

There is general agreement that the virus is transmitted through saliva and nasal secretions. Animals become infected by direct contact with secretions or by exposure to contaminated food or water. It is likely that the nose is the main site of viral entry into the body. Contact experiments in horses have shown that persistently infected animals, not presenting overt disease, such as virus carriers, may represent a source of infection. This observation is of eminent importance for the introduction of BDV and BDV-related infection into stables, herds or breeding colonies without a previous history of BD. There is a great need to develop a laboratory based diagnostic test for the detection of BDV and BDV-related infection as well as carriers. There also is a great need to develop a vaccine against these infections.

The BDV is strictly neurotropic and is disseminated by intra-axonal transport from the site of infection, for example through the olfactory nerve, or other cerebral nerve endings terminating in the mucous membrane of the oropharyngeal region. The virus localizes preferentially in certain parts of the brain such as the grey matter, nucleus niger, hippocampus or olfactory bulb, and may spread centrifugally to the peripheral nerves whereby the virus can reach the ganglia of some organs. Involvement of certain regions of the brain may give certain focal symptoms, for example involvement of the nucleus niger may explain the appearance of motor disorder. The clinical expression of BDV and BDV-related infection is variable and is dependent on the virus strain and the species infected. Hence, diagnosis of BDV infection based on clinical signs is often difficult, unless the infected animal or pet presents the classical symptoms of BD. There is a need to develop a laboratory test to detect infection by this virus to aid in the diagnosis of BDV and BDV-related infection and associated diseases.

Traditionally, horses, sheep and cattle are economically important to agriculture. They are also susceptible to BDV and BDV-related infection. More recently, agricultural husbandry has diversified to include llamas and alpacas for their wool, deer for venison, and ostriches for their meat, feathers and skin. Some of these animals are not indigenous and have to be imported. For example, llamas, alpacas and ostriches imported from South America to the United States, and ostriches imported from Africa to Israel. These animals also are susceptible to BDV and BDV-related infection. Importation of virus carriers into domestic herds or breeding colonies may decimate a young and potentially blooming agriculture business. There is a great need in developing a laboratory test to detect the infected animals at the port of entry. More important, recent evidence that BDV and BDV-related infection in cats may cause a neurologic disease and that BDV may infect humans are disturbing, because it raises the concern that BDV-infected cats may be a viral reservoir of human infections. It is necessary to develop a laboratory test to aid the diagnosis of BDV-associated neurological diseases and other BDV diseases in cats and in other mammals, including humans. It also is important to develop an efficacious vaccine against BDV and BDV-related infection in these animals.

Antibodies or immunoglobulins are complex proteins made by lymphocytes of a host in response to foreign substance, proteins or pathogens called antigens. Antibodies can bind antigens. All antibodies have the same overall shape, but each antibody has unique regions that make it fit to one antigen but not to another. As a result of this specificity, an antibody specific for BDV will not bind to wart virus or influenza virus. A specific antibody is made only after the lymphocyte has encountered the antigen. The specific antibody is released into the blood stream, lymph, colostrum, saliva, cerebral spinal fluid and into the lumens of the gastrointestinal, respiratory and urinary tracts. Hence, detection of specific antibodies to BDV, or to any one of the viral proteins, in any one of these body fluid suggests that the host has been exposed to or infected infected with a BDV.

BRIEF DESCRIPTION OF THE FIGURES

FIG. 2 depicts the nucleotide sequence of ORFx1-FLAG DNA fragment (SEQ ID NO: 5) in the pORFx1-FLAG eukaryotic expression construct (GeneBank Accession Number: 030353). The underlined nucleotides represents the FLAG moiety, not underlined section is the sequence of ORFx1. The not underlined section is provided as SEQ ID NO:7 and is part of the present invention.

FIG. 3 depicts the amino acid sequence of the ORFx1-FLAG (SEQ ID NO:6). The amino acid sequence was derived by computer analysis of the ORFx1-FLAG DNA sequence shown in FIG. 2 by use of the PCgene software (Intellegenetic Suite, CA). One letter symbols for the codons are given. The FLAG amino acids are underlined. Amino acid sequence of ORFx1 encoding a polypeptide p10 is not underlined. The not underlined section is provided as SEQ ID NO:8 and is part of the present invention.

SUMMARY

Figure 1:
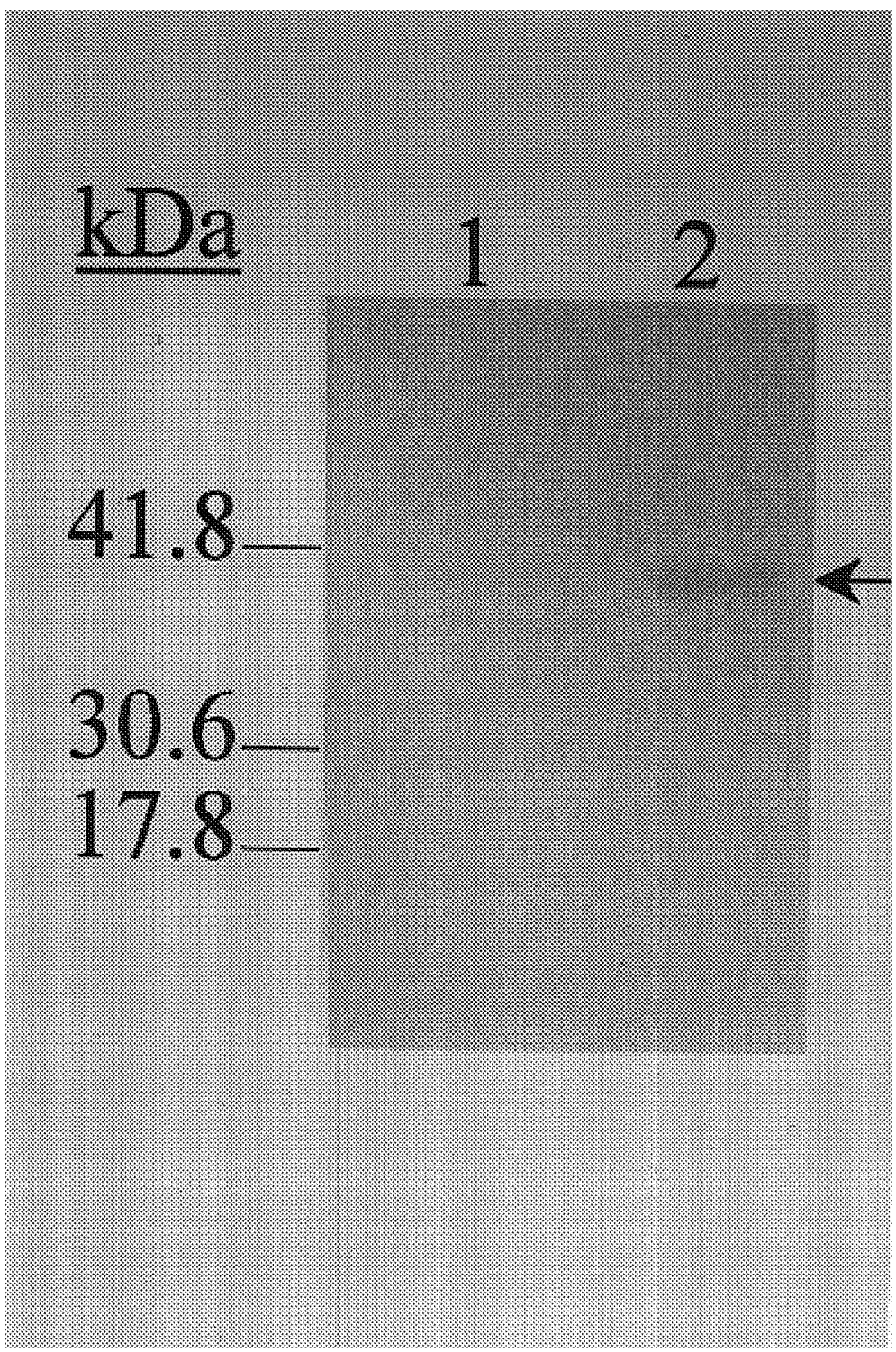
FIG. 1 depicts the identification of the recombinant GST-BDV p10 fusion protein by serum from a rabbit infected with BDV from horse. Western blot analyses of GST protein (lane 1) and GST-BDV p10 fusion protein (lane 2) by use of a serum from a rabbit infected with BDV.

The BDV has not been fully characterized, but overlapping nucleic acid fragments of its genome have been cloned from cells infected by cell-adapted BDV strains. These cell-adapted BDV nucleic acid fragments of its genome had been sequenced to give the complete nucleic acid sequence of the genome (Briese, Proc. Natl. Acad. Sci. USA 91:4362 (1994); Cubitt, J. Virol. 68:1382 (1994)). It is possible to translate the BDV genomic nucleotide sequence into amino acids. From the amino acid sequence, one may predict the number of open reading frames (ORFs) encoding hypothetical proteins. In the case with BDV, the prediction was at least 5 to 6 ORFs, and one of these ORFs, ORFx1, would give a protein of approximately 10 kilodalton (p10). Cloning of BDV mRNAs as cDNAs and expression studies identified a 18 kilodalton, a 24 kilodalton and a 38/40 kilodalton protein as BDV-specific. However, cloning of BDV cDNAs, including one containing the ORFx1, did not provide BDV polypeptide p10 (U.S. Pat. No. 5,654,401 to Clements et al., issued Aug. 5, 1997, and U.S. Pat. No. 5,854,417 to Clements et al., issued Dec. 29, 1998). Hence, from the prior art it was uncertain whether the BDV polypeptide p10 protein actually exists or whether it is an hypothetical protein not produced naturally. In the course of this invention, it was found that the BDV polypeptide p10 is indeed naturally produced.

One aspect of the present invention is a polypeptide having at least one bioactivity of a polypeptide p10 of a Borna Disease Virus.

A second aspect of the present invention is a specific binding member, such as an antibody or polypeptide p40 or polypeptide p24, that binds with at least a portion of a polypeptide p10 of a Borna Disease Virus.

A third aspect of the present invention is a nucleic acid molecule that encodes a polypeptide having at least one bioactivity of a polypeptide of a Borna Disease Virus.

A fourth aspect of the present invention is a test kit that includes at least one of: a polypeptide of the present invention, a specific binding member of the present invention or a nucleic acid molecule of the present invention.

A fifth aspect of the present invention is a vaccine and method of immunization that includes at least one of: a polypeptide of the present invention, a specific binding member of the present invention or a nucleic acid molecule of the present invention.

A sixth aspect of the present invention is a method of diagnosis that includes at least one of: a polypeptide of the present invention, a specific binding member of the present invention or a nucleic acid molecule of the present invention.

A seventh aspect of the present invention is a method of identifying test compounds or bioactivities, preferably test compounds or bioactivities that are useful in the present invention.

DETAILED DESCRIPTION

Definitions

Unless defined otherwise, all technical and scientific terms used herein have the same meaning as commonly understood by one of ordinary skill in the art to which this invention belongs. Generally, the nomenclature used herein and the laboratory procedures in cell culture, chemistry, microbiology, molecular biology, cell science and cell culture described below are well known and commonly employed in the art. Conventional methods are used for these procedures, such as those provided in the art and various general references (Sambrook et al., Molecular Cloning: A Laboratory Manual, 2nd edition, Cold Spring Harbor Press, Cold Spring Harbor, N.Y. (1989)). Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

"Isolated polynucleotide" refers to a polynucleotide of genomic, cDNA, or synthetic origin, or some combination thereof, which by virtue of its origin, the isolated polynucleotide (1) is not associated with the cell in which the isolated polynucleotide is found in nature, or (2) is operably linked to a polynucleotide that it is not linked to in nature. The isolated polynucleotide can optionally be linked to promoters, enhancers, or other regulatory sequences. "Isolated protein" or "isolated polypeptide" refers to a protein or polypeptide of DNA, cDNA, RNA, recombinant RNA, recombinant DNA or synthetic origin, or some combination thereof, which by virtue of its origin the isolated protein or isolated polypeptide (1) is not associated with proteins normally found within nature, or (2) is isolated from the cell in which it normally occurs, or (3) is isolated free of other proteins from the same cellular source, for example, free of cellular proteins), or (4) is expressed by a cell from a different species, or (5) does not occur in nature.

"Polypeptide" is used herein as a generic term to refer to a molecule comprising at least one peptide bond, such as, for example, a protein or a fragment, analogue or active fragment thereof.

"Active fragment" refers to a fragment of a parent molecule, such as an organic molecule, nucleic acid molecule, or polypeptide, or combinations thereof, that retains at least one activity of the parent molecule.

"Naturally occurring" refers to the fact that an object can be found in nature. For example, a polypeptide or polynucleotide sequence that is present in an organism, including viruses, that can be isolated from a source in nature and which has not been intentionally modified by man in the laboratory is naturally occurring.

"Molecular weight" refers to an apparent size estimation under the circumstances and methods used described in the individual examples. The true molecular mass can only be determined after sequencing the full length protein.

"Operably linked" refers to a juxtaposition wherein the components so described are in a relationship permitting them to function in their intended manner. A control sequence operably linked to a coding sequence is ligated in such a way that expression of the coding sequence is achieved under conditions compatible with the control sequences.

"Control sequences" refer to polynucleotide sequences that effect the expression of coding and non-coding sequences to which they are ligated. The nature of such control sequences differs depending upon the host organism; in prokaryotes, such control sequences generally include promoter, ribosomal biding site, and transcription termination sequences; in eukaryotes, generally, such control sequences include promoters and transcription termination sequences. The term control sequences is intended to include components whose presence can influence expression, and can also include additional components whose presence is advantageous, for example, leader sequences and fusion partner sequences.

"Polynucleotide" refers to a polymeric form of nucleotides of a least ten bases in length, either ribonucleotides or deoxynucleotides or a modified from of either type of nucleotide. The term includes single and double stranded forms of DNA or RNA.

"Directly" in the context of a biological process or processes, refers to direct causation of a process that does not require intermediate steps, usually caused by one molecule contacting or binding to another molecule (the same type or different type of molecule). For example, molecule A contacts molecule B, which causes molecule B to exert effect X that is part of a biological process.

"Indirectly" in the context of a biological process or precesses, refers to indirect causation that requires intermediate steps, usually caused by two or more direct steps. For example, molecule A contacts molecule B to exert effect X which in turn causes effect Y.

"Sequence homology" refers to the proportion of base matches between two nucleic acid sequences or the proportion of amino acid matches between two amino acid sequences. When sequence homology is expressed as a percentage, for example 50%, the percentage denotes the proportion of matches of the length of sequences from a desired sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

"Selectively hybridize" refers to detectably and specifically bind. Polynucleotides, oligonucleotides and fragments thereof selectively hybridize to target nucleic acid strands, under hybridization and wash conditions that minimize appreciable amounts of detectable binding to nonspecific nucleic acids. High stringency conditions can be used to achieve selective hybridization conditions as known in the art. Generally, the nucleic acid sequence homology between the polynucleotides, oligonucleotides, and fragments thereof and a nucleic acid sequence of interest will be at least 30%, and more typically and preferably of at least 40%, 50%, 60%, 70%, 80%, 90%, 91%, 92%, 93%, 94%, 95%, 96%, 97%, 98% or 99%.

Hybridization and washing conditions are typically performed at high stringency according to conventional hybridization procedures. Positive clones are isolated and sequenced. For example, a full length polynucleotide sequence can be labeled and used as a hybridization probe to isolate genomic clones from an appropriate target library as they are known in the art. Typical hybridization conditions and methods for screening plaque lifts and other purposes are known in the art (Benton and Davis, Science 196:180 (1978); Sambrook et al., supra, (1989)).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at least 5 (in standard deviation units) using the program ALIGN with the mutation data matrix and a gap penalty of 6 or greater (Dayhoff, in Atlas of Protein Sequence and Structure, National Biomedical Research Foundation, volume 5, pp. 101–110 (1972) and Supplement 2, pp. 1–10). The two sequences or parts thereof are more preferably homologous if their amino acids are greater than or equal to 30% identical when optimally aligned using the ALIGN program.

"Corresponds to" refers to a polynucleotide sequence is homologous (for example is identical, not strictly evolutionarily related) to all or a portion of a reference polynucleotide sequence, or that a polypeptide sequence is identical to all or a portion of a reference polypeptide sequence. In contradistinction, the term "complementary to" is used herein to mean that the complementary sequence will base pair with all or a portion of a reference polynucleotide sequence. For illustration, the nucleotide sequence TATAC corresponds to a reference sequence TATAC and is complementary to a reference sequence GTATA.

The following terms are used to describe the sequence relationships between two or more polynucleotides: "reference sequence," "comparison window," "sequence identity," "percentage of sequence identity," and "substantial identity." A reference sequence is a defined sequence used as a basis for a sequence comparison; a reference sequence can be a subset of a larger sequence, for example, as a segment of a full length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides can each (1) comprise a sequence (for example a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A comparison widow, as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window can comprise additions and deletions (for example, gaps) of 20 percent or less as compared to the reference sequence (which would not comprise additions or deletions) for optimal alignment of the two sequences. Optimal alignment of sequences for aligning a comparison window can be conducted by the local homology algorithm (Smith and Waterman, Adv. Appl. Math., 2:482 (1981)), by the homology alignment algorithm (Needleman and Wunsch, J. Mol. Bio., 48:443 (970)), by the search for similarity method (Pearson and Lipman, Proc. Natl. Acid. Sci. U.S.A. 85:2444 (1988)), by the computerized implementations of these algorithms such as GAP, BESTFIT, FASTA and TFASTA (Wisconsin Genetics Software Page Release 7.0, Genetics Computer Group, Madison, Wis.), or by inspection. Preferably, the best alignment (for example, the result having the highest percentage of homology over the comparison window) generated by the various methods is selected.

"Sequence identity" means that two polynucleotide sequences are identical (for example, on a nucleotide-by-nucleotide basis) over the window of comparison.

"Percentage of sequence identity" is calculated by comparing two optimally aligned sequences over the window of comparison, determining the number of positions at which the identical nucleic acid base occurs in both sequences to yield the number of matched positions, dividing the number of matched positions by the total number of positions in the window of comparison (for example, the window size), and multiplying the result by 100 to yield the percentage of sequence identity.

"Substantial identity" as used herein denotes a characteristic of a polynucleotide sequence, wherein the polynucleotide comprises a sequence that has at least about 30 percent to about 70 percent sequence identity; preferably at least about 60% to about 90% sequence identity; more usually at least about 91%, at least about 92%, at least 93%, at least about 94%, at least about 95%, at least about 96%, at least about 97%, at least about 98% or at least about 99% sequence identity as compared to a reference sequence over a comparison window of at least 20 nucleotide positions, frequently over a window of at least 25 to 50 nucleotides, wherein the percentage of sequence identity is calculated by comparing the reference sequence to the polynucleotide sequence that may include deletions or addition which total 20 percent or less of the reference sequence over the window of comparison.

"Substantial identity" as applied to polypeptides herein means that two peptide sequences, when optimally aligned, such as by the programs GAP or BESTFIT using default gap weights, share at least about 30 percent to about 70 percent sequence identity; preferably at least about 60% to about 90% sequence identity; more usually at least about 91%, at least about 92%, at least 93%, at least about 94%, at least about 95%, at least about 96%, at least about 97%, at least about 98% or at least about 99% sequence identity. Preferably, residue positions, which are not identical, differ by conservative amino acid substitutions.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; a group of amino acids having acidic side chains is aspartic acid and glutamic acid; and a group of amino acids having sulfur-containing side chan is cystein and methionine. Preferred conservative amino acid substitution groups are: valine-leucine-isoleucine; phenylalanine-tyrosine; lysine-arginine; alanine-valine; glutamate-aspartate; and asparagine-glutamine.

"Modulation" refers to the capacity to either enhance or inhibit a functional property of a biological activity or process, for example, enzyme activity or receptor binding. Such enhancement or inhibition may be contingent on the occurrence of a specific event, such as activation of a signal transduction pathway and/or may be manifest only in particular cell types.

"Modulator" refers to a chemical (naturally occurring or non-naturally occurring), such as a biological macromolecule (for example, nucleic acid, protein, non-peptide or organic molecule) or an extract made from biological materials, such as prokaryotes, bacteria, eukaryotes, plants, fungi, multicellular organisms or animals, invertebrates, vertebrates, mammals and humans, including, where appropriate, extracts of: whole organisms or portions of organisms, cells, organs, tissues, fluids, whole cultures or portions of cultures, or environmental samples or portions thereof. Modulators are typically evaluated for potential activity as inhibitors or activators (directly or indirectly) of a biological process or processes (for example, agonist, partial antagonist, partial agonist, antagonist, antineoplastic, cytotoxic, inhibitors of neoplastic transformation or cell proliferation, cell proliferation promoting agents, antiviral agents, antimicrobial agents, antibacterial agents, antibiotics, and the like) by inclusion in assays described herein. The activity of a modulator may be known, unknown or partially known.

"Test chemical" or "test compound" refers to a chemical or extract to be tested by at least one method of the present invention to be a putative modulator. A test chemical is usually not known to bind to the target of interest. "Control test chemical" or "control test compound" refers to a chemical known to bind to the target (for example, a known agonist, antagonist, partial agonist or inverse agonist). Test chemical does not typically include a chemical added to a mixture as a control condition that alters the function of the target to determine signal specificity in an assay. Such control chemicals or conditions include chemicals that (1) non-specifically or substantially disrupt protein structure (for example denaturing agents such as urea or guandium, sulfhydryl reagents such as dithiotritol and beta-mercaptoethanol), (2) generally inhibit cell metabolism (for example mitochondrial uncouples) and (3) non-specifically disrupt electrostatic or hydrophobic interactions of a protein (for example, high salt concentrations or detergents at concentrations sufficient to non-specifically disrupt hydrophobic or electrostatic interactions). The term test chemical also does not typically include chemicals known to be unsuitable for a therapeutic use for a particular indication due to toxicity of the subject. Usually, various predetermined concentrations of test chemicals are used for determining their activity. If the molecular weight of a test chemical is known, the following ranges of concentrations can be used: between about 0.001 micromolar and about 10 millimolar, preferably between about 0.01 micromolar and about 1 millimolar, more preferably between about 0.1 micromolar and about 100 micromolar. When extracts are uses a test chemicals, the concentration of test chemical used can be expressed on a weight to volume basis. Under these circumstances, the following ranges of concentrations can be used: between about 0.001 micrograms/ml and about 1 milligram/ml, preferably between about 0.01 micrograms/ml and about 100 micrograms/ml, and more preferably between about 0.1 micrograms/ml and about 10 micrograms/ml. A test chemical or test compound can have at least one bioactivity.

"Target" refers to a biochemical entity involved in a biological process. Targets are typically proteins that play a useful role in the physiology or biology of an organism. A therapeutic chemical typically binds to a target to alter or modulate its function. As used herein, targets can include, but not be limited to, cell surface receptors, G-proteins, G-protein coupled receptors, kinases, phosphatases, ion channels, lipases, phosholipases, nuclear receptors, intracellular structures, tubules, tubulin, and the like.

"Label" or "labeled" refers to incorporation of a detectable marker, for example by incorporation of a radiolabled compound or attachment to a polypeptide of moieties such as biotin that can be detected by the binding of a section moiety, such as marked avidin. Various methods of labeling polypeptide, nucleic acids, carbohydrates, and other biological or organic molecules are known in the art. Such labels can have a variety of readouts, such as radioactivity, fluorescence, color, chemiluminescence or other readouts known in the art or later developed. The readouts can be based on enzymatic activity, such as beta-galactosidase, beta-lactamase, horseradish peroxidase, alkaline phosphatase, luciferase; radioisotopes such as $^3$H, $^{14}$C, $^{35}$S, $^{125}$I or $^{131}$I); fluorescent proteins, such as green fluorescent proteins; or other fluorescent labels, such as FITC, rhodamine, and lanthanides. Where appropriate, these labels can be the product of the expression of reporter genes, as that term is understood in the art. Examples of reporter genes are beta-lactamase (U.S. Pat. No. 5,741,657 to Tsien et al., issued Apr. 21, 1998) and green fluorescent protein (U.S. Pat. No. 5,777,079 to Tsien et al., issued Jul. 7, 1998; U.S. Pat. No. 5,804,387 to Cormack et al., issued Sep. 8, 1998).

"Substantially pure" refers to an object species or activity that is the predominant species or activity present (for example on a molar basis it is more abundant than any other individual species or activities in the composition) and preferably a substantially purified fraction is a composition wherein the object species or activity comprises at least about 50 percent (on a molar, weight or activity basis) of all macromolecules or activities present. Generally , as substantially pure composition will comprise more than about 80 percent of all macromolecular species or activities present in a composition, more preferably more than about 85%, 90%, 95% and 99%. Most preferably, the object species or activity is purified to essential homogeneity, wherein contaminant species or activities cannot be detected by conventional detection methods) wherein the composition consists essentially of a single macromolecular species or activity. The inventors recognize that an activity may be caused, directly or indirectly, by a single species or a plurality of species within a composition, particularly with extracts.

"Pharmaceutical agent or drug" refers to a chemical, composition or activity capable of inducing a desired therapeutic effect when properly administered by an appropriate dose, regime, route of administration, time and delivery modality.

A "bioactive compound" is a compound or composition that exhibits at least one of following bioactivities: antiviral activity, binding with p40 nucleoprotein N of a BDV, binding with the 24 kd viral phosphoprotein of a BDV, nuclear localization in a eukaryotic cell, at least one epitope, immunogenic activity, T-cell activating activity and antigenic activity. Preferably, a bioactive compound is specific for a BDV, preferably a polypeptide p10 of a BDV, such as, for example, for use as a therapeutic, diagnostic, vaccine or other aspect of the invention for a BDV, but that need not be the case. A bioactive compound can be of any chemical composition such as, for example, a chemical, a small molecule such as a drug, a polypeptide, a nucleic acid, a lipid, a carbohydrate, a nucleic acid molecule such as DNA or RNA or both, or other compound or composition.

A "bioactivity" is a composition or compound that exhibits at least one activity of a bioactive compound.

A "bioactive derivative" is a modification of a bioactive compound or bioactivity that retains at least one characteristic bioactivity of the parent compound.

A "bioactive precursor" is a precursor of a bioactive compound or bioactivity that exhibits at least one characteristic activity of the resulting bioactive compound or bioactivity.

An "antiviral activity" is an activity that reduces the infectivity of at least one virus particle in a sample, such as in a sample including at least one virus, including a subject. An antiviral activity can also prevent or decrease the severity of a viral disease state, such as infection with a BDV and/or the resulting disease state. An antiviral activity can act in any appropriate manner, such as interfering with the attachment, penetration or replication of a virus in any manner; altering the virus particle to render the virus particle less infective or non-infective; or by mounting an immune response, cellular or humoral or both, against a virus or a viral infection, including a virus infected cell.

A "patient" or "subject" is a whole organism in need of treatment, such as a farm animal, companion animal or human. An animal is any animal, but does not include humans.

A "specific binding member" refers to molecules that have specific binding activity towards a polypeptide of the present invention. Such specific binding members can take part in receptor-ligand type reactions and are generally characterized as binding with their binding mate by non-covalent reactions, such as hydrogen bonds, van der Walls interactions, hydrophobic interactions, and the like. A specific binding member can be at least a portion of a molecule, such as a protein, such as p40 nucleoprotein N of BDV or the 24 kd viral phosphoprotein P of BDV, that binds with a polypeptide of the present invention. A specific binding member can also be an immunoglobulin of any class, a polyclonal antibody, a monoclonal antibody, or an active fragment thereof.

"Binds with" in the context of specific binding members, refers to the binding of one specific binding member with its target, such as an antibody binding with a polypeptide of the present invention, and does not infer that the specific binding member will not bind with moieties other than a polypeptide of the present invention.

"Specifically binds with" refers to a specific binding member that detectably binds with a polypeptide of the present invention preferentially or with greater affinity than a moiety other than a polypeptide of the present invention. A specific binding member that specifically binds with one polypeptide of the present invention can also specifically bind with a second polypeptide of the present invention.

"Immobilized" in the context of a test kit refers to a moiety attached to a surface such that the moiety remains substantially immobilized in an aqueous phase as opposed to being substantially mobile in an aqueous phase, such as, for example, in an immunochromatographic device and/or method.

"Vaccine" refers to a composition or compound, that when administered to a subject in an appropriate dose by an appropriate route of administration and an appropriate regime, can prevent the likelihood of the occurrence of the infection or the severity of an infection with a BDV in a non-infected subject through a physiological response, such as an immune response. A vaccine also refers to a composition or compound that, when administered to a subject that has been exposed to a BDV in an appropriate dose by an appropriate route of administration and an appropriate regime, can reduce the likelihood of infection or reduce the severity of infection. A vaccine also refers to a compound or composition that, when administered to a subject that has become infected with a BDV in an appropriate dose by an appropriate route of administration and an appropriate regime, can reduce the severity of infection.

"Borna Disease Virus" or "BDV" refers to a virus that is the etiological agent for "Borna Disease" or "BD" in horses. BDV from horses can infect other animals, such as rats, to cause a "BDV-infection." Viruses that have substantial nucleic acid homology with BDV ("BDV-associated viruses") have been isolated from a variety of species and are considered BDVs. BDV-associated viruses cause "BDV-related infection" which can progress to a "BDV-associated disease" in an appropriate host animal or host cell. "A BDV" includes BDV and BDV-associated viruses. Thus, a BDV can cause a BDV-infection that can progress to BD or a BDV-associated disease. A BDV, a BDV-infection, BD or a BDV-associated disease can be detected using the methods of the present invention. Symptoms of the disease can also be monitored to follow the course of BD or a BDV-associated disease.

Other technical terms used herein have their ordinary meaning in the art that they are used, as exemplified by a variety of technical dictionaries, such as the McGraw-Hill Dictionary of Chemical Terms and the Stedman's Medical Dictionary.

Introduction

The present invention recognizes that a polypeptide of a Borna Disease Virus is expressed as part of the natural course of infectivity of that virus. The present invention relates to polypeptides, specific binding members, nucleic acid molecules, test kits, vaccines, methods of vaccination, vaccinated patients and methods of diagnosis as they relate to a Borna Disease Virus in general, and polypeptide p10 of a Borna Disease Virus in particular.

As a non-limiting introduction to the breath of the present invention, the present invention includes several general and useful aspects, including:

1) a polypeptide having at least one bioactivity of a polypeptide p10 of a Borna Disease Virus;
2) a specific binding member, such as an antibody, that binds with at least a portion of a polypeptide of a Borna Disease Virus;
3) a nucleic acid molecule that encodes a polypeptide having at least one bioactivity of a polypeptide p10 of a Borna Disease Virus;
4) a test kit that includes at least one of a polypeptide of 1), a specific binding member of 2) or a nucleic acid molecule of 3);
5) a vaccine and method of immunization that includes at least one of a polypeptide of 1), a specific binding member of 2) or a nucleic acid molecule of 3);
6) a method of diagnosis including at least one of a polypeptide of 1), a specific binding member of 2) or a nucleic acid molecule of 3); and
7) a method of identifying a test compound or bioactivity, preferably test compounds or bioactivities that are useful in the present invention.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I. A Polypeptide Having at Least One Bioactivity of a Polypeptide p10 of a Borna Disease Virus One aspect of the present invention is a polypeptide, such as a substantially purified or purified polypeptide, having at least one bioactivity of a polypeptide p10 of a Borna Disease Virus (BDV). Bioactivities of a polypeptide of a BDV include, but are not limited to, immunogenic activity, antigenic activity, at least one epitope, localization in a eukaryotic cell, association with p40 nucleoprotein N of BDV and association with the 24 kd viral phosphoprotein P of BDV (see, for example, U.S. application Ser. No. 60/097,901 to Lai et al., filed Aug. 26, 1998; Richt, EP 0791654A1, published Aug. 27, 1997; Wehner et al., J. Gen. Virol. 78:2459–2466 (1997); Malik et al., Virology 258:65–72 (1999)). Such activities can be screened for, determined or confirmed using methods of the present invention or as they are known in the art.

Preferably, a polypeptide of the present invention is between about 10 and about 110 amino acids in length, and more preferably between about 20 amino acids, about 40 amino acids, about 60 amino acids and about 80 amino acids in length and about 30 amino acids, about 50 amino acids, about 70 amino acids, about 90 amino acids and about 110 amino acids in length, but can be of any length and include between about 10 and about 100, between about 20 and about 90, between about 30 and about 80, between about 40 and about 70 and between about 50 and about 60 contiguous amino acids of SEQ ID NO:6. A polypeptide of the present invention can be part of a fusion protein that includes an amino acid molecule of interest operably linked to a polypeptide of the present invention.

The polypeptide of the present invention can be encoded by portions of nucleic acid molecules that were not known to encode a polypeptide p10 (see, for example, U.S. Pat. No. 5,654,401 to Clements et al., issued Aug. 5, 1997; Cubitt et al., J. Virol. 68:1382–1396 (1994); Schwemmie et al., J. Biol. Chem. 273:9007–9012 (1996); WO 96/21020 to Lipkin et al., published Jul. 11, 1996; WO 98/30238 to de la Torre, published Jul. 16, 1998). The regions of nucleic acid molecules that encode a polypeptide p10 or a polypeptide of the present invention can be identified by comparing the nucleic acid sequences of the present invention with nucleic acid molecules that are suspected to encode a polypeptide p10 or a polypeptide of the present invention. The structure of the open reading frame that encodes a polypeptide p10 or polypeptide of the present invention as disclosed herein can be used to establish the activity of the encoded polypeptide. Isolated nucleic acid molecules that encode a polypeptide of the present invention but are not the full length nucleic acid molecule of a BDV or a cDNA copy thereof can be made using methods set forth in the Examples. The activity of the polypeptide can be confirmed by expressing the encoded polypeptide and confirming the activity thereof using methods of the present invention. The present invention includes polypeptides encoded by a nucleic acid that has substantial identity with at least a portion of such nucleic acid sequence, that selectively hybridizes with at least a portion of such nucleic acid sequence, or that encodes a conserved amino acid substitution relative to such nucleic acid sequence. The present invention also included polypeptides that have substantial identity with or have conservative amino acid substitutions relative to such nucleic acid sequences. Examples of such polypeptides of the present invention include SEQ ID NO:15 (portion of accession number pir//B37475, Pyper et al., Virology 195:229–238 (1993)), SEQ ID NO:16 (portion of accession number pir//JQ1294, Richt et al., J. Gen. Virol. 72 (Pt. 9) 2251–2255 (1991)), SEQ ID NO:17 (portion of accession number emb/CAB45670.1/(AJ246860)), SEQ ID NO:18 (portion of emb/CAB45669.1/(AJ246859)), SEQ ID NO:19 (portion of accession number emb/CAB45672.1/(AJ246862)) and SEQ ID NO:20 (portion of accession number emb/CAB45668.1/(AJ246858)).

Preferably, a polypeptide of the present invention comprises at least one bioactivity of the polypeptide encoded by the nucleic acid sequence of SEQ ID NO:5, nucleic acid molecules that have substantial identity with at least a portion of the nucleic acid sequence of SEQ ID NO:5, nucleic acid molecules that selectively hybridizes with at least a portion of the nucleic acid sequence of SEQ ID NO:5, and nucleic acid molecules that encode conservative amino acid substitutions of at least a portion of the nucleic acid sequence of SEQ ID NO:5. Preferably, the polypeptide has a molecular weight of about 10 kd and is encoded by SEQ ID NO:5, but that need not be the case. Preferably, the polypeptide of the present invention binds with at least one antibody that binds with a polypeptide p10 of a Borna Disease Virus, but that need not be the case.

Preferably, a polypeptide of the present invention includes at least a portion of the amino acid sequence of SEQ ID NO:6, has substantial identity with at least a portion of the amino acid sequence of SEQ ID NO:6, or has at least one conserved amino acid substitution of at least a portion of the amino acid sequence of SEQ ID NO:6. Preferably, the polypeptide of the present invention binds with at least one antibody that binds with a polypeptide p10 of a Borna Disease Virus.

Polypeptides of the present invention can be made using recognized methods, such as by recombinant methods as they are known in the art (see, Sambrook et al., supra, (1989)) or by digesting proteins or polypeptides. For example, nucleic acid molecules encoding or suspected of encoding a polypeptide of the present invention can be cloned into expression vectors that are transfected into appropriate host cells where the nucleic acid molecules are expressed. The resulting polypeptides can be optionally purified and their activity confirmed using methods of the present invention or as they are known in the art. Alternatively, the in vivo activity of polypeptides can be confirmed using methods of the present invention or as they are known in the art.

The present invention also includes fusion proteins that include a polypeptide of the present invention. For example, a polypeptide of the present invention can be fused with a polypeptide of interest, such as, for example, a tag such as an epitope tag (such as, for example FLAG) that allows the fusion protein to be readily purified, or a cellular localization sequence as they are known in the art to direct a polypeptide of the present invention to a selected cellular location, such as a membrane or nucleus. Such fusion proteins can be made using methods known in the art and as described herein, such as using molecular cloning methods (see, Sambrook et al., supra (1989)). A polypeptide of interest can be any polypeptide.

II. A Specific Binding Member That Binds With at Least a Portion of a Polypeptide p10 of a Borna Disease Virus Another aspect of the present invention is a specific binding member that binds with a polypeptide of the present invention and can be substantially purified or purified. The specific binding member can be any specific binding member, but is preferably at least a portion of an immunoglobulin, the p40 nucleoprotein N of a BDV, or the 24 kd viral phosphoprotein P of a BDV. Such immunoglobulins can be of any class or subclass of immunoglobulin and can be a polyclonal or monoclonal preparation, including monoclonal or polyclonal antibodies that specifically bind with a polypeptide of the present invention.

Specific binding members of the present invention can be made and identified using methods known in the art. For example, fragments of proteins such as the p40 protein or the phophoprotein P of a BDV can be made using recombinant methods or digestion of protein preparations. These fragments can be screened for their ability to bind and specifically bind with a polypeptide of the present invention using specific binding reactions as they are known in the art, such as using detectably labeled specific binding reagents and formats for receptor ligand interactions as they are known in the art.

When the specific binding member is an antibody or an active fragment thereof, then any appropriate method of making antibody preparations, such as polyclonal and monoclonal antibody preparations, can be used such as they are known in the art (see, Harrow, Antibodies, a Laboratory Manual, Cold Spring Harbor Press (1988)). The binding of such antibody preparations to a polypeptide of the present invention can be screened, determined and confirmed using methods known in the art, such as using ELISAs or other appropriate formats known in the art (see, for example, direct non-competitive assays on a solid phase (U.S. Pat. Nos. 4,187,075 and 4,497,900); Competitive binding on a solid phase (U.S. Pat. Nos. 4,134,792, 4,478,946, 4,092,408, and 4,478,946); Sequential saturation (U.S. Pat. Nos. 4,134, 792, 4,271,140); Displacement or release assays (U.S. Pat. Nos. 4,120,945, 4,256,725 and 4,434,236); One-site immunometric on solid phase (U.S. Pat. Nos. 4,134,792 and 4,670,383); Sandwich assays (U.S. Pat. No. 4,134,792 and U.S. Pat. No. 4,478,946)).

III. A Nucleic Acid Molecule That Encodes a Polypeptide Having at Least One Bioactivity of a Polypeptide p10 of a Borna Disease Virus The present invention also includes a nucleic acid molecule, including a substantially purified or purified nucleic acid molecule, encoding a polypeptide comprising at least one bioactivity of a polypeptide p10. Preferably, the nucleic acid molecule encodes at least a portion of the amino acid sequence of SEQ ID NO:6 or SEQ ID NO:8 and includes at least a portion of the nucleic acid sequence of SEQ ID NO:5 or SEQ ID NO:7. Such nucleic acid molecules can be DNA, RNA, single stranded, double stranded, or any combination thereof The nucleic acid molecule of the present invention also includes nucleic acid molecules that selectively hybridize with at least a portion of the nucleic acid sequence of SEQ ID NO:5 or that encode at least one conservative amino acid substitution of at least a portion of the amino acid sequence of SEQ ID NO:6. Preferably, the nucleic acid molecule of the present invention encodes the full length sequence of SEQ ID NO:6 or a substantial portion thereof and is encoded by the nucleic acid sequence of SEQ ID NO:5 or a substantial portion thereof, such that a polypeptide resulting from the expression of the nucleic acid molecule would have a molecular weight between about 9.5 kd and about 10.5 kd. Preferably, the nucleic acid molecule encodes a polypeptide that binds with, and preferably specifically binds with, at least one specific binding member that binds with a polypeptide p10 of a Borna Disease Virus.

A nucleic acid molecule of the present invention can also be a portion of nucleic acid molecules that were not known to encode a polypeptide p10 (see, for example, U.S. Pat. No. 5,654,401 to Clements et al., issued Aug. 5, 1997; Cubitt et al., J. Virol. 68:1382–1396 (1994); Schwemmie et al., J. Biol. Chem. 273:9007–9012 (1996); WO 96/21020 to Lipkin et al., published Jul. 11, 1996; WO 98/30238 to de la Torre, published Jul. 16, 1998). Regions of nucleic acid molecules that encode a polypeptide p10 or a polypeptide of the present invention can be identified by comparing the nucleic acid sequences of the present invention with nucleic acid molecules that are suspected to encode a polypeptide p10 or a polypeptide of the present invention. The structure of the open reading frame that encodes a polypeptide p10 or polypeptide of the present invention as disclosed herein can be used to establish the activity of the encoded polypeptide. Isolated nucleic acid molecules that encode a polypeptide of the present invention but are not the full length nucleic acid molecule of a BDV or a cDNA copy thereof can be made using methods set forth in the Examples. The activity of the polypeptide can be confirmed by expressing the encoded polypeptide and confirming the activity thereof using methods of the present invention. The present invention includes nucleic acid molecules that have substantial identity with at least a portion of such nucleic acid sequence, that selectively hybridizes with at least a portion of such nucleic acid sequence, or that encode a conserved amino acid substitution relative to such nucleic acid sequence. Examples of such nucleic acid molecules of the present invention include SEQ ID NO:9 (portion of accession number gb/L27077/BDVSEQ, Cubitt et al., J. Virol. 68:1382–1396 (1994)), SEQ ID NO:10 (portion of accession number dbj/D10473/BDVP24, Richt et al. J. Gen. Virol. 72 (Pt. 9) 2251–2255 (1991)), SEQ ID NO:11 (portion of accession number gb/S62821/S62821, Pyper et al. Virology 195:229–238 (1993)), SEQ ID NO:12 (portion of accession number gb/U04608/BDU04608, Briese et al. Proc. Natl. Acad. Sci. U.S.A. 91:4362–4366 (1994)), SEQ ID NO:13 (portion of accession number emb/X60701/NCBDV24) and SEQ ID NO:14 (portion of accession number gb/AF094478.1/AF094478)).

Nucleic acid molecules of the present invention can be made using methods known in the art and described herein (see, Sambrook et al, supra, (1989)). For example, nucleic acid molecules of the present invention can be identified and isolated using PCR methodologies, including RT-PCR, and sequenced using established methods such that their homologies can be determined. The ability of one nucleic acid molecule to hybridize with another can be determined through experimentation under a variety of stringencies, or can be estimated based on their length and G:C contents. Alterations of identified sequences can be made using routine methods, such as mutagenesis, RT-PCR or other PCR methods (see, Sambrook et al., supra, (1989)).

The nucleic acid molecule of the present invention can be operably linked to at least one control sequence such that the nucleic acid molecule can be expressed in a cell or ex vivo, such as using transcription and translation systems as they are available commercially. The choice of such expression control sequences is dependent upon the cell or system to be used to express the nucleic acid molecule. For example, if a prokaryotic cell such as E. coli is to be used to express the nucleic acid molecule, then appropriate prokaryotic expression control sequences would be used. If a eukaryotic cell, such as a human cell, is to be used to express the nucleic acid molecule, then appropriate eukaryotic expression control sequences, such as LTRs or CMV promoters, would be used. Such constructs can be made using methods known in the art. Such nucleic acid molecules can be in any form, such as in a plasmid or in a linear form.

The nucleic acid molecule of the present invention, with or without the expression control sequence, can be provided in a vector. Such vectors include plasmids and linear molecules or can be provided in a viral vector as they are known in the art and appropriate for a cell to be transfected, such as, for example, a phage, cosmid, retrovirus, vaccinia, adenovirus or adenoassociated virus.

Such nucleic acid molecules, with or without expression control sequences and present or not present in a vector, can be inserted into a cell using established methods. Such nucleic acid molecules can be extrachromosomal or be integrated into the genome of the cell. For example, viral vectors can introduce nucleic acid molecules into a cell as part of their routine biology. Lipofection, microbalistics and electroporation can also be used to introduce nucleic acid molecules into a cell. In addition, certain cells, in particular muscle cells and epidermal cells, especially in vivo, can routinely take up and express naked nucleic acid molecules.

Preferably, the cell does not normally include a nucleic acid molecule of the present invention or express a polypeptide of the present invention, but that need not be the case. For example a cell that expresses a relatively low amount of a polypeptide of the present invention can be made to express relatively higher amounts of a polypeptide once transfected with a nucleic acid of the present invention.

Cells that express a polypeptide of the present invention can be screened for and selected using a variety of methods, including those set forth in the present invention. For example, immunoassays, such as western blots, can be used to identify cell lysates that include a polypeptide of the present invention. In addition, immunocytochemistry can be used to identify and localize a polypeptide of the present invention on or within a cell. Furthermore, in situ hybridization method, such as FISH, can be used to identify and localize nucleic acid molecules within a cell and hybridization methods can be used to identify nucleic acid molecules, either DNA or RNA, from cellular preparations.

IV. A Test Kit Including at Least One of a Polypeptide, Specific Binding Member or Nucleic Acid Molecule of the Present Invention Another aspect of the present invention are test kits that can be used to detect a polypeptide, specific binding member or nucleic acid molecule of the present invention. The test kits can be used to determine whether a subject has been exposed to, infected with or vaccinated against a BDV.
Polypeptides Another aspect of the present invention is a test kit for detecting specific binding members that bind with a polypeptide of the present invention that are useful, for example, for detecting BDV infection, exposure or vaccination in a subject. The test kit can have any number of reagents and hardware, but preferably comprises at least one polypeptide of the present invention, wherein said polypeptide can be provided immobilized on a solid support or not so immobilized.

The kit of the present invention can take any appropriate configuration that uses a polypeptide to detect specific binding members, particularly antibodies, that bind thereto. For example, the polypeptide of the present invention can be immobilized on a solid support, this combination being useful in an appropriate specific binding assay. In this instance, the polypeptide can be immobilized on beads (such as latex or magnetic), bibulous structures (such as filter paper), membrane structure (such as nitrocellulose or a variety of polymers) or solid platform.

When the polypeptide is immobilized on beads, the beads can be used in an agglutination specific binding assay as they are known in the art. When the polypeptide is immobilized on a bibulous structure or membrane structure, this bibulous structure or membrane structure can be used in an chromatographic type specific binding assay as they are known in the art. This type of assay format is well known in the art and forms the basis of a variety of immunodiagnostics, such as the well-known pregnancy tests. When the polypeptide is immobilized on a solid platform, such as a solid platform that comprises at least one polymer (such as polystyrene), such as a multi-well platform, such as a microtiter plate, this structure can be used to perform a variety of specific binding reactions, such as immunoassays, as they are known in the art.

A variety of specific binding reaction formats are known in the art, many of which use detectably labeled specific binding reagents, such as detectably labeled antibodies or antigens. Such formats are represented by the following: Direct non-competitive assay on a solid support (U.S. Pat. Nos. 4,187,075 and 4,497,900); Competitive binding of a solid support (U.S. Pat. Nos. 4,134,792, 3,654,090, 4,478, 946, 4,092,408, 4,478,946, 4,271,140, 4,288,237, 4,490,473, 4,243,749, 4,298,685, 3,839,153, 4,048,298, 4,271,140); Sequential saturation (U.S. Pat. Nos. 4,134,792, 4,271,140, 4,048,298); Displacement or release assay (U.S. Pat. Nos. 4,120,945, 4,256,725, 4,388,295, 4,434,236); One-site immunometric on solid support (U.S. Pat. Nos. 4,134,792, 3,654,090, 4,134,792, 3,850,752, 4,134,752, 4,134,792, 4,670,383, 4,332,495, 4,034,074; GB 2,084,317 and EP 0,177,191); Sandwich assays (U.S. Pat. Nos. 4,234,792, 4,376,110, 4,478,946, 4,271,140, 4,034,074, 4,271,140, 4,474,892, 4,230,683, 4,288,237, 4,098,876, 4,376,110, 4,486,530, 4,271,140, 4,343,896; see also Turgeon, Immunology and Serology in Laboratory Medicine, C.V. Mosby Co., St. Louis, 1990).

A polypeptide of the present invention can be provided free, directly immobilized to a solid support or indirectly immobilized on a solid support. A free polypeptide or a polypeptide indirectly immobilized on a solid support can be provided as part of a cell, such as a cell that expresses the polypeptide, either as part of a BDV natural infection (such as from a sample from a subject), from cells infected with a BDV in culture or cells that express a polypeptide of the present invention as a result of genetic manipulation as discussed herein. The cell can be a prokaryotic or eukaryotic cell. When immobilized, the cell can be immobilized using a variety of methods, such as fixing, entrapment (such as in a filter) or on a surface coated with a substance that attaches cells (such as fibronectin or other extracellular matrix protein or polypeptides).

The test kit of the present invention can also include at least one specific binding reagent, such as an antibody or antigen, that is useful in the present invention. The at least one specific binding reagent is preferably an antibody and can be detectably labeled. Such specific binding reagents can be used to detect the binding of antigen to antibody in a variety of formats that use indirect or direct detection methods, such as a detectably labeled anti-antibody used in an indirect immunoassay.

Test kits of the present invention can also include additional reagents and hardware that can be used to practice the invention. For example, a test kit can include a housing to hold a chromatographic test strip and can also provide instructions for use of the test kit, preferably to perform at least one method of the present invention. Such instructions can be in such detail and language as appropriate for the intended operator of the test kit. Such instructions can be provided as a separate item, or be provided on or within a container. The test kit can be provided in one or more containers, including a container useful for packaging, transport and marketing. The test kit can be provided in a variety of packaging formats, including hermetically sealed containers to aid in preserving the integrity and activity of elements of a test kit, such as a test strip, or reagents of the present invention.

Specific Binding Members

Another aspect of the present invention is a test kit for detecting polypeptides that bind with a specific binding member of the present invention (such as an antibody) that are useful, for example, for detecting infection with, exposure to or vaccination against a BVD in a subject, including but not limited to BD, BDV infection, BDV-related infection and BDV-associated disease. The test kit can have any number of reagents and hardware, but preferably comprises at least one specific binding member of the present invention, wherein said specific binding member can be provided immobilized on a solid support or not so immobilized.

The kit of the present invention can take any appropriate configuration that uses a specific binding member to detect polypeptides that bind thereto. For example, a specific binding member of the present invention can be immobilized on a solid support, this combination being useful in an appropriate specific binding assay. In this instance, the specific binding member can be immobilized to beads (such as latex or magnetic), bibulous structures (such as filter paper), membrane structure (such as nitrocellulose or a variety of polymers) or solid platform.

When the specific binding member is immobilized on beads, the beads can be used in an agglutination specific binding assay as they are known in the art. When the specific binding member is immobilized on a bibulous structure or membrane structure, this bibulous structure or membrane structure can be used in an chromatographic type specific binding assay as they are known in the art. This type of assay format is well known in the art and forms the basis of a variety of immunodiagnostics, such as the well-known pregnancy tests. When the specific binding member is immobilized on a solid platform, such as a solid platform that comprises at least one polymer (such as polystyrene), such as a multi-well platform, such as a microtiter plate, this structure can be used to perform a variety of specific binding reactions, such as immunoassays, as they are known in the art.

A variety of specific binding reaction formats are known in the art, many of which use detectably labeled specific binding reagents, such as detectably labeled antibodies or antigens. Such formats are represented by the following: Direct non-competitive assay on a solid support (U.S. Pat. Nos. 4,187,075 and 4,497,900); Competitive binding of a solid support (U.S. Pat. Nos. 4,134,792, 3,654,090, 4,478, 946, 4,092,408, 4,478,946, 4,271,140, 4,288,237, 4,490,473, 4,243,749, 4,298,685, 3,839,153, 4,048,298, 4,271,140); Sequential saturation (U.S. Pat. Nos. 4,134,792, 4,271,140, 4,048,298); Displacement or release assay (U.S. Pat. Nos. 4,120,945, 4,256,725, 4,388,295, 4,434,236); One-site immunometric on solid support (U.S. Pat. Nos. 4,134,792, 3,654,090, 4,134,792, 3,850,752, 4,134,752, 4,134,792, 4,670,383, 4,332,495, 4,034,074; GB 2,084,317 and EP 0,177,191); Sandwich assays (U.S. Pat. Nos. 4,234,792, 4,376,110, 4,478,946, 4,271,140, 4,034,074, 4,271,140, 4,474,892, 4,230,683, 4,288,237, 4,098,876, 4,376,110, 4,486,530, 4,271,140, 4,343,896; see also Turgeon, Immunology and Serology in Laboratory Medicine, C.V. Mosby Co., St. Louis, 1990).

The test kit of the present invention can also include a second specific binding reagent, such as an antibody or an antigen, that is useful in the present invention. The second specific binding reagent is preferably and antibody or an antigen and can be detectably labeled. Such specific binding reagents can be used to detect the binding of antigen to antibody in a variety of formats that use indirect or direct detection methods, such as a detectably labeled antigen used in an a direct or indirect specific binding reaction.

Test kits of the present invention can also include additional reagents and hardware that can be used to practice the invention. For example, a test kit can include a housing to hold a chromatographic test strip and can also provide instructions for use of the test kit, preferably to perform at least one method of the present invention. Such instructions can be in such detail and language as appropriate for the intended operator of the test kit. Such instructions can be provided as a separate item, or be provided on or within a container. The test kit can be provided in one or more containers, including a container useful for packaging, transport and marketing. The test kit can be provided in a variety of packaging formats, including hermetically sealed containers to aid in preserving the integrity and activity of elements of a test kit, such as a test strip, including reagents of the present invention.

Nucleic Acid Molecules

Another aspect of the present invention is a test kit for detecting a nucleic acid molecule of the present invention that is useful, for example, for detecting infection with, exposure to or vaccination against a BDV in a subject, including but not limited to BD, BDV infection, BDV-related infection or BDV-associated disease. The test kit can have any number of reagents and hardware, but preferably comprises at least one nucleic acid molecule of the present invention, wherein the nucleic acid molecule can be provided immobilized on a solid support or not so immobilized.

The kit of the present invention can take any appropriate configuration that uses a nucleic acid molecule to detect another nucleic acid molecule. For example, one or more nucleic acid molecules of the present invention can be immobilized on a solid support, this combination being useful in an appropriate hybridization assay. In this instance, the nucleic acid molecule can be immobilized onto a variety of solid supports, such as membrane structures (such as nitrocellulose or a variety of polymers such as with northern blot, Southern blot, dot-blot or slot-blot technologies), silicon (such as with gene chip technologies) or a solid platform. The nucleic acid molecules can be immobilized using methods known in the art for a particular solid substrate. Such immobilized nucleic acid molecules can take the form of an array and can be derived from cells infected with a BDV and/or cells not infected with a BDV in order to form the basis for differential display assays for BDV infections.

A nucleic acid molecule used to detect the presence of another nucleic acid molecule can be detectably labeled with a variety of appropriate labels such that a hybridization event can be detected and monitored. Appropriate detectable labels and methods of labeling nucleic acid molecules with them are known in the art.

In this aspect of the present invention, the nucleic acid molecule, either immobilized or not immobilized or detectably labeled or not delectably labeled, can be DNA or RNA. As is known in the art, single stranded sense/antisense RNA can hybridize with single stranded antisense/sense RNA or single stranded antisense/sense DNA. Also, single stranded sense/antisense DNA can hybridize with single stranded antisense/sense RNA or single stranded antisense/sense DNA.

Furthermore, the present invention includes polymerase chain reaction (PCR) methods including RT-PCR that can be used to amplify and optionally detect a nucleic acid molecule of the present invention in a sample, such as in a cell. PCR methods, including RT-PCR, as they are known in the art, use primers to amplify a target sequence. The primer sequences of the present invention, or primers that can function to selectively amplify a nucleic acid sequence of the present invention, are considered part of the present invention. The confirmation of the operability of a set of PCR primers to amplify a target sequence can be made using established PCR methods and those set forth herein.

Amplified target sequences can be detected directly using, for example, real-time quantitative PCR (Heid et al., Genome Res. 6:986–994 (1996); Gibson et al., Genome Research 6:995–1001 (1996), Freeman et al., BioTechniques 26:112–125 (1999)). Alternatively, the amplified sequences can be detected by hybridization with complementary sequences, such as, for example, using solid-phase hybridization reactions and detectably labeled nucleic acid sequences.

Test kits of the present invention can also include additional reagents and hardware that can be used to practice the invention. For example, a test kit can include a housing to hold a membrane that includes immobilized nucleic acid molecules and can also provide instructions for use of the test kit, preferably to perform at least one method of the present invention. Such instructions can be in such detail and language as appropriate for the intended operator of the test kit. Such instructions can be provided as a separate item, or be provided on or within a container. The test kit can be provided in one or more containers, including a container useful for packaging, transport and marketing. The test kit can be provided in a variety of packaging formats, including hermetically sealed containers to aid in preserving the integrity and activity of elements of a test kit, such as a test strip, including reagents of the present invention.

V. A Vaccine and Method of Immunization Including At Least One of a Polypeptide, Specific Binding Member or Nucleic Acid Molecule of the Present Invention Another aspect of the present invention is a polypeptide, specific binding member or nucleic acid molecule of the present invention that can be used as a vaccine for a BDV. The present invention also includes animals vaccinated using the compositions or methods of the present invention. Although different sections are provided herein for different classifications of vaccines, methods discussed in the various sections relating to immunity, vaccination and vaccines are applicable to the other sections.

Polypeptides

A vaccine of the present invention can include a polypeptide of the present invention. The polypeptide can be provided in a pharmaceutically acceptable carrier and can optionally be provided with an appropriate adjuvant. The vaccine can be provided in at least one container in a single dose or in multiple doses. The dose, route of administration and regime of vaccine administration are such that the desired response is obtained. An effective amount, dose and regime of a vaccine can be determined by administering a vaccine via a variety of routes in a variety of amount by a variety of regimes to a subject and monitoring the response obtained by such administration.

The ability of a vaccine to stimulate a humoral and/or cellular immune response to the vaccine and/or a BDV indicates that a vaccine and its method of administration are efficacious. Such cellular and humoral cellular responses can be determined using methods known in the art (see, for example, Clark, The Experimental Foundations of Modern Immunology, John Wiley & Sons, New York (1980); Turgeon, supra, (1990); Upjohn, Immunology, a SCOPE publication, Upjohn Company, Kalamozoo, Mich. (1991); Roitt et al., Immunology, third edition, Mosby, St. Louis, (1993)).

After the administration of a vaccine, a subject can be challenged with a BDV to establish that the vaccine can prevent or reduce the severity of infection with a BDV. In the alternative, if the subject has been exposed to or become infected with a BDV, the subject can be administered a vaccine in order to establish that the vaccine can prevent or reduce the severity of such an infection.

Vaccines can be administered by any appropriate route of administration, including, for example, intramuscularly, subcutaneously, orally or by other acceptable routes of administration. Vaccine regimes can include a single or plural administrations of a vaccine at a single or different doses at a single or multiple routes of administration.

The method of the present invention includes administering a vaccine of the present invention to a subject, such as an animal and/or a human. The immune status of the subject as to the presence of a humoral and/or cellular response to the vaccine and/or a BDV can optionally be determined or confirmed using methods discussed herein. The present invention also includes a subject, particularly a non-human subject or non-human animal, that has been administered a vaccine of the present invention, particularly such a subject that has immunity to a BDV. Immunity in this instance refers to a subject that exhibits a humoral and/or cellular immune response to the vaccine and/or BDV.

Specific Binding Members

The present invention also includes vaccines that include a specific binding member of the present invention, preferably preparations that include at least one antibody or an active fragment thereof. Preferably, the antibody preparation is of a type that is not itself substantially antigenic to the recipient of the vaccine, such as "humanized" antibodies being administered to humans rather than mouse antibodies being administered to humans. Such "humanized" antibodies can be made using methods known in the art.

Vaccine compositions that include such specific binding members are most useful for "passive" immunity after a subject has been exposed to a BDV such that the likelihood of infection or severity of infection are reduced. The dose, route of administration and regime of vaccination can be determined using methods discussed herein and as are known in the art, such as for passive immunization against hepatitis B virus as is known in the art. The method of the present invention includes administering a vaccine of the present invention to a subject, such as an animal and/or a human. The immune status of the subject as to the presence of a humoral and/or cellular immune response to the vaccine and/or a BDV can optionally be determined or confirmed using methods discussed herein. The present invention also includes a subject, particularly a non-human subject or non-human animal, that has been administered a vaccine of the present invention, preferably such a subject that has immunity to a BDV. Immunity in this instance refers to a subject that exhibits a humoral and/or cellular immune response to the vaccine and/or a BDV.

Nucleic Acid Molecules

The present invention also includes vaccines that include at least one nucleic acid molecule of the present invention. Nucleic acid molecules administered to subject either alone or in a vector, such as a viral vector, can be taken up by cells and expressed such that a polypeptide of the present invention is produced by such cells. The polypeptide can be secreted by the cell or be presented on the surface of the cell, depending on the characteristics of the polypeptide. For example, the nucleic acid molecule can encode a protein such as a fusion protein that is secreted by the cell and thus provides a dose of vaccine over time that can stimulate the production of a cellular or humoral response to the vaccine. Alternatively, a fusion protein that has sequences that target the fusion protein to an outer membrane can give rise to a strong cellular immune response to the vaccine.

Naked nucleic acid vaccines have been used to vaccinate subjects against a variety of etiological agents. In this aspect of the present invention, naked nucleic acid molecules devoid of vectors such as viral vectors are injected into a tissue, preferably muscle, where they are taken up by the tissue and expressed. The naked nucleic acid molecules preferably include expression control sequences appropriate for the expression of the nucleic acid molecule of the present invention. The naked nucleic acid molecule tends to reside extra-chromosomally and thus the nucleic acid molecule tends to be expressed only transiently. Alternatively, the nucleic acid molecule can become integrated into the host cell's genome and be expressed for extended periods of time and can be constitutively expressed. Such integration can be site directed by, for example, homologous recombination (see, for example, WO 94/24301 to Smith et al., published Oct. 27, 1994) or be random (see, for example, WO 98/13353 to Whitney et al., published Apr. 2, 1998).

Nucleic acid vaccines can also be present in a vector such as a viral vector, such as retroviral vectors, vaccinia vectors, adenoviral vectors or adenoassociated vectors. These vectors can be targeted to particular tissues or to tissues in general. Upon infection of target cells, the nucleic acids of the present invention can be expressed in such cells as described in the section for naked nucleic acid vaccines. Like the naked nucleic acid vaccines, the nucleic acids of the present invention can be optionally operably linked to expression control sequences and can optionally remain extrachromosomal or become integrated into a cell's genome. Such integration can be directed (see, for example, WO 94/24301 to Smith et al., published Oct. 27, 1994) or be random (see, for example, WO 98/13353 to Whitney et al., published Apr. 2, 1998).

The vaccines of the present invention can be of any nucleic acid structure. For example, the vaccines can be single stranded, double stranded or triple stranded and can be of DNA, RNA or a combination thereof. The nucleotides can be of any con figuration, such as linear, circular, relaxed or supercoiled. The nucleic acid can be provided in an appropriate pharmaceutically acceptable carrier and can optionally be provided with an appropriate adjuvant in an appropriate amount.

Vaccines can be administered by any appropriate route of administration, including, for example, intramuscularly, subcutaneously, orally or by other acceptable routes of administration. Vaccine regimes can include a single or plural administrations of a vaccine at a single or different doses at a single or multiple routes of administration.

The method of the present invention includes administering a vaccine of the present invention to a subject, such as an animal and/or a human. The immune status of the subject as to the presence of a humoral and/or cellular response to the vaccine and/or a BDV can optionally be determined or confirmed using methods discussed herein. The present invention also includes a subject, particularly a non-human subject or non-human animal, that has been administered a vaccine of the present invention, particularly such a subject that has immunity to a BDV. Immunity in this instance refers to a subject that exhibits a humoral and/or cellular immune response to the vaccine and/or a BDV.

VI. A Method of Diagnosis Including at Least One of a Polypeptide, Specific Binding Member or Nucleic Acid Molecule of the Present Invention The present invention also includes methods of determining whether a subject has been exposed to, infected with or vaccinated against a BDV. This aspect of the present invention uses samples from a subject. Such samples can be any sample from the subject, such as any tissue, fluid, excretion, secretion or combination thereof. Preferably, the sample is a sample that would be expected to contain anti-BDV antibodies, a BDV virus, cells infected with a BDV, polypeptides from a BDV or nucleic-acids from a BDV. The sample can be assayed as is, or can be prepared prior to an assay being performed. Such preparation methods include dilution, concentration, extraction or other method of preparation suitable for a particular assay format.

Polypeptides

The present invention also includes a method of testing a subject to determine whether the subject has a been exposed to, infected with or vaccinated against a BDV. The method includes the steps of: providing a sample from a subject; contacting the sample with a polypeptide of the present invention; and detecting the binding of the polypeptide with the sample. In this aspect of the present invention, the sample is being tested to determine whether the sample includes anti-BDV antibodies that bind with a polypeptide of the present invention. In this aspect of the present invention, blood, serum, body secretions or other samples that contain relatively high amounts of antibodies of any class or subclass are preferred. Serum is a preferred sample for this aspect of the present invention. The sample is contacted with a polypeptide of the present invention, such as a polypeptide of the present invention immobilized upon a solid support, and the binding of the antibody to the polypeptide detected. Preferably, a detectably labeled anti-antibody is used to detect antibody bound to the polypeptide, but any appropriate format can be used, particularly those discussed herein.

The amount of antibody in a sample can be determined by comparing the amount of detectable label bound to the polypeptide with a standard or control prepared for the assay. The control can include assay readouts for positive, negative and questionable results. The control can be provided as part of the assay method, such as positive and negative controls as they are appropriate and known in the art. Preferably, the control includes a standard curve that provides a quantitative or semi-quantitative readout for the method, although qualitative readouts are also considered part of the present invention.

Specific Binding Members

The present invention also includes a method of testing a subject to determine whether the subject has a been exposed to, infected with or vaccinated against a BDV. The method includes the steps of: providing a sample from a subject; contacting the sample with a specific binding member of the invention, preferably an antibody; and detecting the binding of the specific binding member with said sample.

In this aspect of the present invention, the sample is being tested to determine whether the sample includes peptides from a BDV that bind with a specific binding member of the present invention. In this aspect of the present invention, blood, serum, CNS fluid, body secretions or other samples such as tissues and cells, particularly tissues and cells of neural or blood origin, that contain relatively high amounts of polypeptides from a BDV, particularly polypeptide p10, are preferred. The sample is contacted with a specific binding member of the present invention, such as an antibody of the present invention immobilized upon a solid support, and the binding of the antibody to the polypeptide detected. Preferably, a detectably labeled antibody is used to detect antigen bound to the immobilized specific binding member in a sandwich-type format, but any appropriate format can be used, particularly those discussed herein.

Alternatively, a sample, such as a sample of blood, serum, CNS fluid, body secretions or other samples such as tissues and cells, particularly tissues and cells of neural and blood origin, is immobilized upon a solid support, such as a glass slide or plastic microtiter well, and a specific binding member of the present invention is contacted with the sample. Preferably, the specific binding member is detectably labeled, but that need not be the only format to be utilized and any appropriate assay format is contemplated.

The amount of polypeptide from a BDV in a sample can be determined by comparing the amount of detected bound labels to the specific binding member with a standard or control prepared for the assay. The control can include assay readouts for positive, negative and questionable results. The control can be provided as part of the assay method, such as positive and negative controls as they are appropriate and known in the art. Preferably, the control includes a standard curve that provides a quantitative or semi-quantitative readout for the method, although qualitative readouts are also considered part of the present invention.

Nucleic Acid Molecules

The present invention also includes a method of testing a subject to determine whether the subject has been exposed to, infected with or vaccinated against a BDV. The method includes the steps of: providing a sample from a subject; contacting the sample with a nucleic acid molecule of the present invention; and detecting the binding of said nucleic acid molecule with said sample.

In this aspect of the present invention, the sample is being tested to determine whether the sample includes nucleic acids, such as nucleic acids from a BDV, that hybridize with a nucleic acid of the present invention. In this aspect of the present invention, blood, serum, CNS fluid, body secretions or other samples such as tissues and cells, particularly cells of neural or blood origin, that contain relatively high amounts of nucleic acids from a BDV are preferred. The nucleic acid molecule of the present invention is contacted with the sample. Preferably, the nucleic acids in the sample have been immobilized upon a solid support, such as a membrane, and the nucleic acid molecule of the present invention is detectably labeled, but that need not be the only format to be utilized and any appropriate assay format is contemplated.

Alternatively, nucleic acids from a BDV in a sample can be amplified using appropriate nucleic acid amplification procedures, such as PCR and appropriate primers. The amplification product can be detected directly using established methods, or can be detected using hybridization methods described herein.

The amount of nucleic acid from a BDV in a sample can be determined by comparing the amount of detectable label bound to the nucleic acids in the sample with a standard or control prepared for the assay. The control can include assay readouts for positive, negative and questionable results. The control can be provided as part of the assay method, such as positive and negative controls as they are appropriate and known in the art. Preferably, the control includes a standard curve that provides a quantitative or semi-quantitative readout for the method, although qualitative readouts are also considered part of the present invention.

VII. A Method For Identifying Test Compounds and Bioactivities

The present invention also includes a method for identifying a test compound or a bioactivity. This method includes contacting a sample comprising at least one cell infected with a BDV with a test compound and monitoring the course of infection with a BDV in the at least one cell. Alternatively, at least one cell is contacted with a test compound, the contacted at least one cell is then contacted with a BDV and the course of infection with a BDV in the at least one cell is monitored. Alternatively, at least one BDV is contacted with a test compound, the contacted BDV is then contacted with at least one cell and the course of infection with a BDV in the at least one cell is monitored. Alternatively, at least one cell is contacted with at least one BDV and at least one test chemical and the course of infection with a BDV in the at least one cell is monitored. Preferably, the results obtained by this method are compared with the results obtained using appropriate controls, such as, for example, cells that are infected with a BDV but have not been contacted with a test compound and cells that have not been infected with a BDV and have not been contacted with a test compound. Appropriate controls can be determined by the skilled artisan based on the particular assay format used.

The at least one cell used in this method is preferably a cell that is permissive to infection with a BDV. Such cells are known in the art and are set forth herein in the Examples. Test compounds that modulate the course of infection with a BDV, particularly by slowing or preventing the course of the infection with a BDV, have presumptive therapeutic activity to prevent or treat infection with a BDV.

The course of infection with a BDV in the at least one cell can be monitored using any appropriate method. Preferably, methods that use a detectable label are used so that the readout can be used in automated methods, such as in high throughput screening methods. For example, the presence or amount of a polypeptide from a BDV or nucleic acid molecule from a BDV can be detected in the cells or cell lysates using methods described herein.

For example, polypeptides from a BDV can be detected in cells using immunohistochemical methods, preferably using at least one specific binding member that is detectably labeled. Alternatively, cell lysates can be prepared and polypeptides from a BDV detected therein using immunoassay formats, including western blot analysis as described herein, preferably using detectably labeled specific binding members. Alternatively, nucleic acids from a BDV can be detected in cells using in situ hybridization methods, preferably using detectably labeled nucleic acid molecules as probes. Furthermore, nucleic acids from a BDV in cell lysates can be detected using, for example, PCR amplification methods or dot blot or slot blot analysis as described herein.

Any appropriate polypeptide from a BDV or nucleic acid from a BDV can be used in these methods to monitor the course of infection with a BDV. Preferably, nucleic acids from a BDV that encode a polypeptide p10 or specific binding members that bind with a polypeptide p10 are used, more preferably detectably labeled nucleic acids or detectably labeled specific binding members.

The present invention includes a compound or composition identified by a method of the present invention.

Preferably, such compound or composition prevents infection with a BDV of a cell, decreases the severity of infection with a BDV, alters the time course of infection with a BDV or prevents the production of viable BDV from an infection with a BDV or results in fewer viable BDV from being produced from an infection with a BDV. However, other mechanisms of action of a compound or composition may be identified and the inventors expressly do not wish to be limited to any mode of action or mechanism.

An identified compound or composition can be provided in a pharmaceutically acceptable carrier and alternatively in a pharmaceutically effective amount. Such compounds or compositions can be provided in appropriate packaging for pharmaceutical compositions and provide instructions for use thereof.

Systems

The present invention also includes a system that can be used to practice at least one method of the present invention. Such systems can include a storage structure, a dispensation structure, a detector structure, and a computing structure, each of which can be separate or combined. A storage structure stores at least one reagent for use in a method, such as cells, buffers and test compounds. The dispensation structure dispenses such reagents into a receptacle for use in the method, such as a solid support such as a microtiter plate. The detector structure includes a detector to detect the readout of the method, such as radioactivity, chromogens or fluorescence. The computing structure is directly or indirectly connected to the detection structure and obtains data therefrom. The computing structure comprises computer hardware and software to process the data obtained from the detector structure and can also monitor and control the storage structure, dispensation structure and detector structure (see, U.S. Pat. No. 5,670,113 to Akong, issued Sep. 23, 1997; WO 98/55231 to Pham et al., published Dec. 10, 1998; WO 98/52047 to Shumate et al. published Nov. 19, 1998).

Preferably, a system of the present invention includes at least one polypeptide, cell, specific binding member, nucleic acid or other compound or reagent of the present invention. Such compounds or reagents of the present invention can be used in at least one method of the present invention, or in other methods, for use in a system of the present invention.

Pharmacology and Toxicity of Test Compounds

The structure of a test compound can be determined or confirmed by methods known in the art, such as mass spectroscopy. For test compounds stored for extended periods of time under a variety of conditions, the structure, activity and potency thereof can be confirmed.

Identified test compounds can be evaluated for a particular activity using art-recognized methods and those disclosed herein. For example, if an identified test compound is found to have anticancer cell activity in vitro, then the test compound would have presumptive pharmacological properties as a chemotherapeutic to treat cancer. Such nexuses are known in the art for several disease states, and more are expected to be discovered over time. Based on such nexuses, appropriate confirmatory in vitro and in vivo models of pharmacological activity, and toxicology, and be selected and performed. The methods described herein can also be used to assess pharmacological selectivity and specificity, and toxicity.

Identified test compounds can be evaluated for toxicological effects using known methods (see, Lu, Basic Toxicology, Fundamentals, Target Organs, and Risk Assessment, Hemisphere Publishing Corp., Washington (1985); U.S. Pat. Nos.; 5,196,313 to Culbreth (issued Mar. 23, 1993) and U.S. Pat. No. 5,567,952 to Benet (issued Oct. 22, 1996)). For example, toxicology of a test compound can be established by determining in vitro toxicity towards a cell line, such as a mammalian, for example human, cell line. Test compounds can be treated with, for example, tissue extracts, such as preparations of liver, such as microsomal preparations, to determine increased or decreased toxicological properties of the test compound after being metabolized by a whole organism. The results of these types of studies are predictive of toxicological properties of chemicals in animals, such as mammals, including humans.

Alternatively, or in addition to these in vitro studies, the toxicological properties of a test compound in an animal model, such as mice, rats, rabbits, dogs or monkeys, can be determined using established methods (see, Lu, supra (1985); and Creasey, Drug Disposition in Humans, The Basis of Clinical Pharmacology, Oxford University Press, Oxford (1979)). Depending on the toxicity, target organ, tissue, locus and presumptive mechanism of the test compound, the skilled artisan would not be burdened to determine appropriate doses, $LD_{50}$ values, routes of administration and regimes that would be appropriate to determine the toxicological properties of the test compound. In addition to animal models, human clinical trials can be performed following established procedures, such as those set forth by the United States Food and Drug Administration (USFDA) or equivalents of other governments. These toxicity studies provide the basis for determining the efficacy of a test compound in vivo.

Efficacy of Test Compounds

Efficacy of a test compound can be established using several art recognized methods, such as in vitro methods, animal models or human clinical trials (see, Creasey, supra (1979)). Recognized in vitro models exist for several diseases or conditions. For example, the ability of a compound or composition to extend the life-span of HIV-infected cells in vitro is recognized as an acceptable model to identify chemicals expected to be efficacious to treat HIV infection or AIDS (see, Daluge et al., Antimicro. Agents Chemother. 41:1082–1093 (1995)). Furthermore, the ability of cyclosporin A (CsA) to prevent proliferation of T-cells in vitro has been established as an acceptable model to identify chemicals expected to be efficacious as immunosuppressants (see, Suthanthiran et al., supra (1996)). For nearly every class of therapeutic, disease or condition, an acceptable in vitro or animal model is available. In addition, these in vitro methods can use tissue extracts, such as preparations of liver, such as microsomal preparations, to provide a reliable indication of the effects of metabolism on a test compound. Similarly, acceptable animal models can be used to establish efficacy of test compound to treat various diseases or conditions. For example, the rabbit knee is an accepted model for testing agents for efficacy in treating arthritis (see, Shaw and Lacy, J. Bone Joint Surg. (Br.) 55:197–205 (1973)). Hydrocortisone, which is approved for use in humans to treat arthritis, is efficacious in this model which confirms the validity of this model (see, McDonough, Phys. Ther. 62:835–839 (1982)). When choosing an appropriate model to determine efficacy of test compounds, the skilled artisan can be guided by the state of the art to choose an appropriate model, doses and route of administration, regime and endpoint and as such would not be unduly burdened.

In addition to animal models, human clinical trials can be used to determine the efficacy of test compounds. The USFDA, or equivalent governmental agencies, have established procedures for such studies.

Selectivity of Test Compounds

The in vitro and in vivo methods described above also establish the selectivity of a candidate modulator. It is recognized that chemicals can modulate a wide variety of biological processes or be selective. Panels of cells as they are known in the art can be used to determine the specificity of the a test compound (WO 98/13353 to Whitney et al., published Apr. 2, 1998). Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a test compound can be established in vitro by testing the toxicity and effect of a test compound on a plurality of cell lines that exhibit a variety of cellular pathways and sensitivities. The data obtained from these in vitro toxicity studies can be extended to animal model studies, including human clinical trials, to determine toxicity, efficacy and selectivity of a test compound.

The selectivity, specificity and toxicology, as well as the general pharmacology, of a test compound can be often improved by generating additional test chemicals based on the structure/property relationship of a test compound originally identified as having activity. Test compounds can be modified to improve various properties, such as affinity, life-time in blood, toxicology, specificity and membrane permeability. Such refined test compounds can be subjected to additional assays as they are known in the art or described herein. Methods for generating and analyzing such compounds or compositions are known in the art, such as U.S. Pat. No. 5,574,656 to Agrafiotis et al.

Pharmaceutical Compositions

The present invention also encompasses a test compound in a pharmaceutical composition comprising a pharmaceutically acceptable carrier prepared for storage and preferably subsequent administration, which has a pharmaceutically effective amount of the test compound in a pharmaceutically acceptable carrier or diluent. Acceptable carriers or diluents for therapeutic use are well known in the pharmaceutical art, and are described, for example, in Remington's Pharmaceutical Sciences, Mack Publishing Co., (A. R. Gennaro edit. (1985)). Preservatives, stabilizers, dyes and even flavoring agents can be provided in the pharmaceutical composition. For example, sodium benzoate, sorbic acid and esters of p-hydroxybenzoic acid can be added as preservatives. In addition, antioxidants and suspending agents can be used.

The test compounds of the present invention can be formulated and used as tablets, capsules or elixirs for oral administration; suppositories for rectal administration; sterile solutions, suspensions or injectable administration; and the like. Injectables can be prepared in conventional forms either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride and the like. In addition, if desired, the injectable pharmaceutical compositions can contain minor amounts of nontoxic auxiliary substances, such as wetting agents, pH buffering agents and the like. If desired, absorption enhancing preparations, such as liposomes, can be used.

The pharmaceutically effective amount of a test compound required as a dose will depend on the route of administration, the type of animal or patient being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the present invention, the pharmaceutical compositions can be used alone or in combination with one another, or in combination with other therapeutic or diagnostic agents. These products can be utilized in vivo, preferably in a mammalian patient, preferably in a human, or in vitro. In employing them in vivo, the pharmaceutical compositions can be administered to the patient in a variety of ways, including parenterally, intravenously, subcutaneously, intramuscularly, colonically, rectally, nasally or intraperitoneally, employing a variety of dosage forms. Such methods can also be used in testing the activity of test compounds in vivo.

As will be readily apparent to one skilled in the art, the useful in vivo dosage to be administered and the particular mode of administration will vary depending upon the age, weight and type of patient being treated, the particular pharmaceutical composition employed, and the specific use for which the pharmaceutical composition is employed. The determination of effective dosage levels, that is the dose levels necessary to achieve the desired result, can be accomplished by one skilled in the art using routine methods as discussed above. Typically, human clinical applications of products are commenced at lower dosage levels, with dosage level being increased until the desired effect is achieved. Alternatively, acceptable in vitro studies can be used to establish useful doses and routes of administration of the test compounds.

In non-human animal studies, applications of the pharmaceutical compositions are commenced at higher dose levels, with the dosage being decreased until the desired effect is no longer achieved or adverse side effects are reduced of disappear. The dosage for the test compounds of the present invention can range broadly depending upon the desired affects, the therapeutic indication, route of administration and purity and activity of the test compound. Typically, dosages can be between about 1 ng/kg and about 10 micrograms/kg, preferably between about 10 ng/kg and about 1 mg/kg, more preferably between about 100 ng/kg and about 100 micrograms/kg, and most preferably between about 1 microgram/kg and about 10 micrograms/kg.

The exact formulation, route of administration and dosage can be chosen by the individual physician in view of the patient's condition (see, Fingle et al., in The Pharmacological Basis of Therapeutics (1975)). It should be noted that the attending physician would know how to and when to terminate, interrupt or adjust administration due to toxicity, organ dysfunction or other adverse effects. Conversely, the attending physician would also know to adjust treatment to higher levels if the clinical response were not adequate. The magnitude of an administrated does in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight and response of the individual patient, including those for veterinary applications.

Depending on the specific conditions being treated, such pharmaceutical compositions can be formulated and administered systemically or locally. Techniques for formation and administration can be found in Remington's Pharmaceutical Sciences, 18th Ed., Mack Publishing Co., Easton, Pa. (1990). Suitable routes of administration can include oral, rectal, transdermal, otic, ocular, vaginal, transmucosal or intestinal administration; parenteral delivery, including intramuscular, subcutaneous, intramedullary injections, as well as intrathecal, direct intraventricular, intravenous, intraperitoneal, intranasal, or intraocular injections.

For injection, the pharmaceutical compositions of the present invention can be formulated in aqueous solutions, preferably in physiologically compatible buffers such as Hanks' solution, Ringer's solution or physiological saline buffer. For such transmucosal administration, penetrans appropriate to the barrier to be permeated are used in the formulation. Such penetrans are generally known in the art. Use of pharmaceutically acceptable carriers to formulate the pharmaceutical compositions herein disclosed for the practice of the invention into dosages suitable for systemic administration is within the scope of the invention. With proper choice of carrier and suitable manufacturing practice, the compositions of the present invention, in particular, those formulation as solutions, can be administered parenterally, such as by intravenous injection. The pharmaceutical compositions can be formulated readily using pharmaceutically acceptable carriers well known in the art into dosages suitable for oral administrations. Such carriers enable the bioactive compounds and bioactivities of the invention to be formulated as tables, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Substantially all molecules present in an aqueous solution at the time of liposome formation are incorporated into or within the liposomes thus formed. The liposomal contents are both protected from the external microenvironment and, because liposomes fuse will cell membranes, are efficiently delivered into the cell cytoplasm. Additionally, due to their hydrophobicity, small organic molecules can be directly administered intracellularly.

Pharmaceutical compositions suitable for use in the present invention include compositions wherein the active ingredients are contained in an effective amount to achieve its intended purpose. Determination of the effective amount of a pharmaceutical composition is well within the capability of those skilled in the art, especially in light of the detailed disclosure provided herein. In addition to the active ingredients, these pharmaceutical compositions can contain suitable pharmaceutically acceptable carriers comprising excipients and auxiliaries which facilitate processing of the active chemicals into preparations which can be used pharmaceutically. The preparations formulated for oral administration may be in the form of tables, dragees, capsules or solutions. The pharmaceutical compositions of the present invention can be manufactured in a manner that is itself known, for example by means of conventional mixing, dissolving, granulating, dragee-making, emulsifying, encapsulating, entrapping or lyophilizing processes. Pharmaceutical formulations for parenteral administration include aqueous solutions of active chemicals in water-soluble form.

Additionally, suspensions of the active chemicals may be prepared as appropriate oily injection suspensions. Suitable lipophilic solvents or vehicles include fatty oils such as sesame oil, or synthetic fatty acid esters, such as ethyl oleate or triglycerides or liposomes. Aqueous injection suspensions may contain substances what increase the viscosity of the suspension, such as sodium carboxymethyl cellulose, sorbitol or dextran. Optionally, the suspension can also contain suitable stabilizers or agents that increase the solubility of the chemicals to allow for the preparation of highly concentrated solutions.

Pharmaceutical compositions for oral use can be obtained by combining the active chemicals with solid excipient, optionally grinding a resulting mixture, and processing the mixture of granules, after adding suitable auxiliaries, if desired, to obtain tables or dragee cores. Suitable excipients are, in particular, fillers such as sugars, including lactose, sucrose, mannitol or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose and/or polyvinylpyrrolidone. If desired, disintegrating agents can be added, such as the cross-linked polyvinyl pyrolidone, agar, alginic acid or a salt thereof such as sodium alginate. Dragee cores can be provided with suitable coatings. Dyes or pigments can be added to the tablets or dragee coatings for identification or to characterize different combinations of active doses.

The test compounds of the present invention, and pharmaceutical compositions that include such test compounds are useful for treating a variety of ailments in a patient, including a human. A patient in need of such treatment can be provided a test compound of the present invention, preferably in a pharmacological composition in an effective amount to reduce the number or infectivity of viruses in said patient. The amount, dosage, route of administration, regime and endpoint can all be determined using the procedures described herein.

EXAMPLES

General Materials and Methods

Suitable starting material for the process of this invention are mammalian cells infected with a BDV. Examples of these include brains from animals infected with a BDV from the field or from the laboratory, and mammalian cell lines such as Madin-Darby canine kidney (MDCK) cells from the American Type Culture Collection, Rockville, Md., accession number CCL-34, and infected with a BDV in the laboratory. Total RNA may be isolated from the BDV-infected cells by standard techniques described in standard texts, including "Molecular Cloning—A Laboratory Manual" Second Edition by J. Sambrook, E. F. Fritsch and T. Mariatis, Cold Spring Harbor Laboratory Press 1989. For cloning of the BDV ORFx1, oligonucleotide primers that hybridize to either ends of the ORFx1 are used in the reverse transcription-polymerase chain reaction (RT-PCR) to synthesize and amplify ORFx1 cDNA from the total RNA template. For easy cloning of the amplified ORFx1 cDNA into a vector for protein expression, it is desirable to have unique restriction enzyme sites present at the 5'-end of each oligonucleotide primer. Desirable pairs of primers (SEQ ID NO:1 and SEQ ID NO:2, respectively) include:

Primer 1=5'-TGT GAATTCAATGAGTTCCGACCTCCGG-3' (SEQ ID NO:1);

Primer 2=5'-TGC CTCGAGTCATTCGATAGCTGCTCCC-3' (SEQ ID NO:2)

or (SEQ ID NO:3 and SEQ ID NO:4, respectively)

Primer 1=5'-CGG GAATTCACCATGGGTTCCGACCTCCGG-3' (SEQ ID NO:3),

Primer 2=5'-TGC CTCGAGTCACTTGTCATCGTCGTCCTTGTAGT CTCGATAGCTGCTCCC-3' (SEQ ID NO:4)

The unique enzyme sites are underlined. In the preferred embodiment of the present invention, RT-PCR can be performed by use of a RT-PCR kit (Strategene, La Jolla, Calif.)

in a thermal cycler (Perkin-Elmer Corp., Foster City, Calif.). Typically, between 20 and 35 cycles of thermal reaction may be performed. Generally, 30 cycles, each consisting of denaturation at 94° C. for 2 mins, annealing at 54° C. for 1 min and extension at 72° C. for 2 mins, followed by a final extension at 72° C. for 10 mins are desirable. The RT-PCR product is digested with the appropriate restriction enzyme and unidirectionally ligated into a suitable expression vector by standard molecular biology techniques. Prokaryotic expression vectors and eukaryotic expression vectors are suitable vectors. Generally, suitable expression vectors include but are not limited to the pGEX series of prokaryotic expression vectors from Pharmacia (Piscataway, N.J.) catalog numbers 27-4805-01, 27-4801-01, 27-4803-01, 47-4580-01, 27-4581-01, 27-4583-01 to 27-4587-01, the pET series of prokaryotic expression vectors from Novagen (Madison, Wis.) catalog numbers 69409-1, 69413-1, 69415-1, 69405-1, 69407-1, 69667-1, 69668-1, 69669-1, 69726-1, 69727-1, 69678-1, 69760-1, 69762-1, 69764-1, 69766-1, 69768-1, 69773-1, 69775-1, 69777-1, 69868-1, 69875-1, 69907-1, 69953-1, 69018-1, 69055-1, and the pcDNA series of eukaryotic expression vectors from Invitrogen (San Diego, Calif.) catalog numbers V308-20, V490-20, V460-20, V790-20, V750-20. The recombinant constructs can then be used to express the desired BDV polypeptide p10 in a prokaryote by transformation into competent *E. coli* (Example 1) or in a eukaryote by transfection of mammalian cells (Example 2). The cDNAs in the recombinant construct can be sequenced by standard molecular biology techniques (Sanger, Proc. Natl. Acad. Sci. USA 74:5463 (1977). The nucleotide sequence (SEQ ID NO: 5 of FIG. 2, and GeneBank Accession number 030353) of the cDNA inserts is 98% homologous to the nucleotide sequence from nucleotide 1223 to 1486 of the previously reported He/80-1 clone of horse-derived BDV (homology being determined using Intelligenetics pcGene program, version 6.85). The amino acid sequence of the recombinant p10 deduced from the cDNA sequence is given as SEQ ID NO: 6 in FIG. 3.

Figure 4:
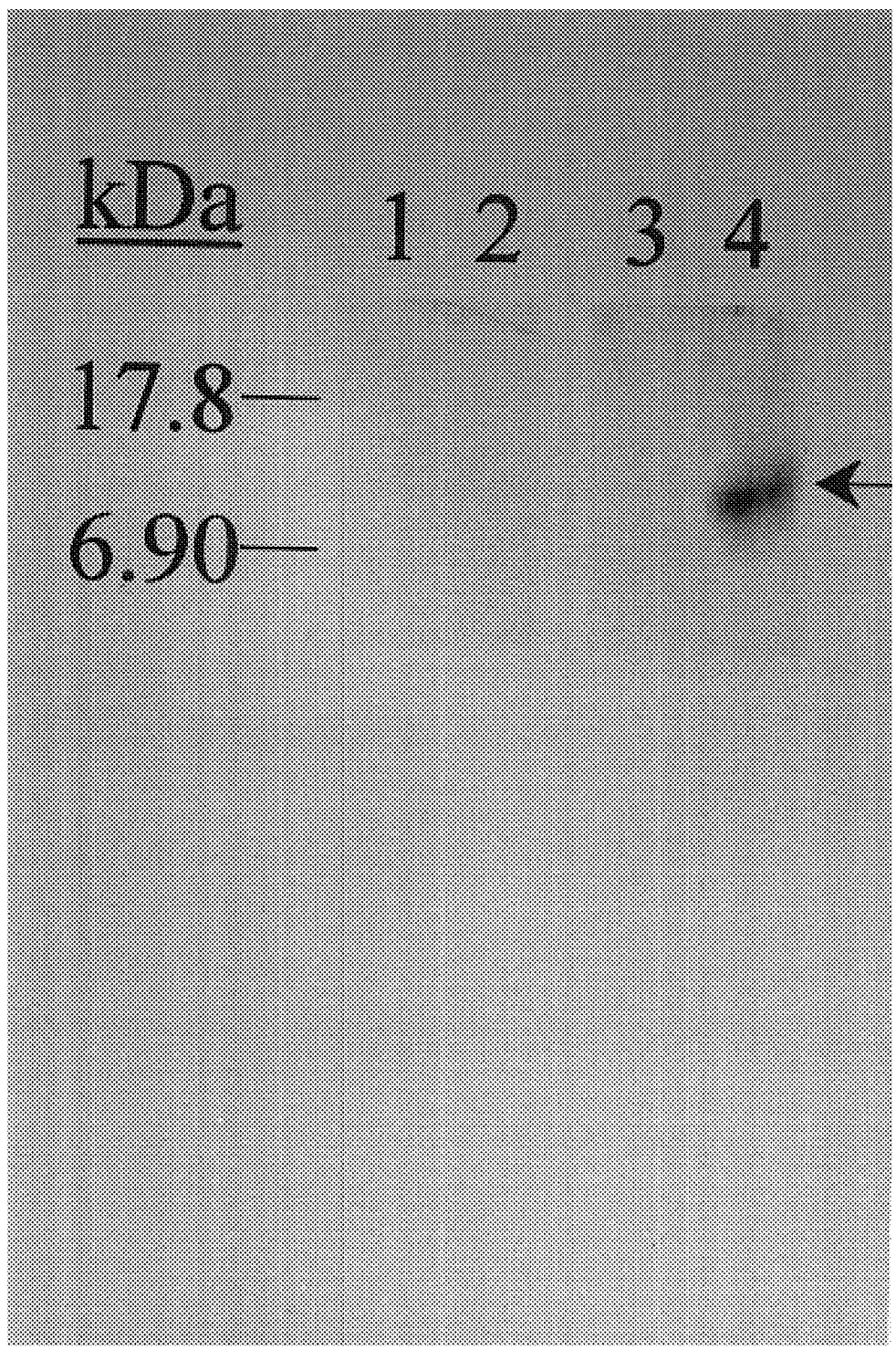
FIG. 4 depicts the specificity of the anti-BDV polypeptide p10 rabbit antiserum to a BDV polypeptide p10. Total protein cell-free lysate from the rat glial cell C6 (ATCC accession number CCL-107) (lanes 1 and 2) and from the BDV-infected C6BV cells (lanes 3 and 4) were tested by western blot against sera collected from a rabbit before immunization (lanes 1 and 3) and after immunization (lanes 2 and 4) with the affinity column-purified GST-BDV polypeptide p10 fusion protein. A protein band with an apparent molecular weight of approximately 10 kilodalton was identified by the immune serum in the protein sample from the infected cells.
Figure 5:
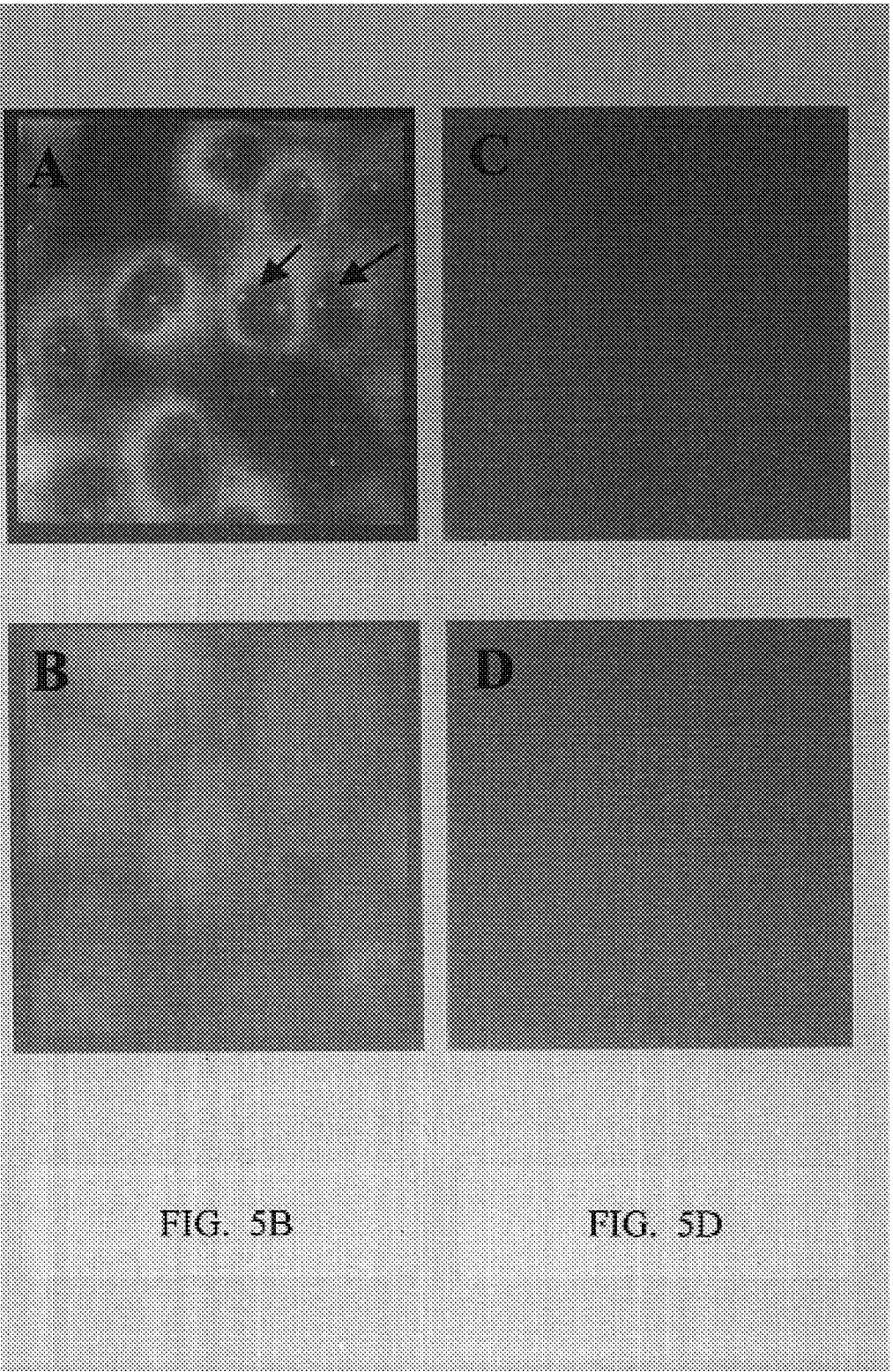
FIG. 5A, FIG. 5B, FIG. 5C and FIG. 5D depict the specificity of the anti-BDV polypeptide p10 rabbit antiserum to BDV. The Madin-Darby canine kidney cells MDCK (ATCC accession number CCL-34) infected (panels A and C) and not infected (panels B and D) with BDV were stained in immunofluorescence assays (IFA) by the anti-BDV polypeptide p10 rabbit serum (panels A and B) prepared as described in Example 3, and previously tested as shown in FIG. 4. Only the infected cells were stained (panel A). The staining was observed in the nucleus and in the cytoplasm of the infected cells. The preimmune serum did not stain the infected (panel C) or the non-infected (panel D) cells.

It is clear from prior art that polyclonal and monoclonal antibodies can be raised against a protein, polypeptide or peptide. Injection of a foreign protein into an animal will raise specific antibodies to this protein. This invention teaches that the purified polypeptide p10 recombinant fusion protein can be used to raise specific antibodies by injection into experimental animals (Example 3), and the resultant specific polyclonal antiserum can be used to detect BDV and its associated viruses in cells infected with the virus (FIG. 4 and FIG. 5). This detection of BDV polypeptide p10 by the specific polyclonal antiserum in BDV-infected cells, but not in non-infected cells shows that BDV polypeptide p10 is a naturally occurring protein of BDV. The present invention also teaches the use of this BDV polypeptide p10-specific antiserum to detect cells infected with BDV or BDV-associated viruses, because non-infected cells do not react with the antiserum. This BDV polypeptide p10-specific antiserum can be used as a diagnostic to identify the presence of BDV in animal or human specimens/cells. From prior art, it also is clear that by use of tissue cultured cells BDV can be isolated from infected animals or humans (Lundgren, J. gen. Virol. 76:2215 (1995); Bode, Mol. Psychiatry 1:200 (1996)), and the presence of the virus in the cultured cells can be identified by the an antiserum. The BDV polypeptide p10-specific antiserum given in Example 3 can, therefore, be used as a diagnostic to identify the presence of BDV in tissue cultured cells inoculated with human or animal specimens. The identification can be carried out by immunological techniques known in the art, and may include, but not limited to, immunofluorescence, immunochemistry, immunoprecipitation and Western blot.

The present invention also concerns testkits for determining antibodies directed against BDV polypeptide p10 as a marker for BDV and BDV-associated infection. The immunological detection can be accomplished by techniques known in the art. These may include but are not limited to immunofluorescence, immunochemistry, radioimmunoassay, ELISA, Western blots, radioimmunoprecipitation assays and immunoagglutination tests. The particular techniques are practiced as are known in the art. Purified polypeptide p10 protein can be used in specific determination of a BDV infection and/or BDV-associated disease. Example 4 is just one of the examples demonstrating how such a determination of BDV infection can be accomplished. In the preferred embodiments of the present invention, the kits comprise a solid support with BDV polypeptide p10 protein. The solid support may include a matrix material, polystyrene or other plastic beads or supports to which BVD polypeptide p10 is readily bound, such as a matrix material for performing immunoprecipitation and immunoaffinity chromatography; beads for performing immune agglutination tests, microtiter dishes for performing the ELISA; or a dipstick for performing a sandwich-type assay. The solid support may be a nylon/nitrocellulose membrane to which the p10 protein can be deposited and linked for performing Western blots as shown in Example 4. The solid support also can be in a form of animal cells transfected by an eukaryotic vector expressing p10 (Examples 2 and FIG. 6) for immunofluorescence or immunochemistry tests. Other reagents for carrying out the assay may be present in the kit, these reagents include but not limited to enzymes, dyes, chromogenic substrates etc. for detecting the antibody-antigen complexes.

It is anticipated within the scope of this invention that methods utilizing nucleic acid hybridization techniques also can be used to determine the presence of BDV or a BDV associated virus. These can be performed as they are known in the art. Hybridizations can be performed electrophoretically on separated RNA species isolated from cells or tissues, as in the Northern techniques. Alternatively, hybridizations can be performed in situ. Other techniques known to the art can be performed by use of specific nucleotide probes specific to BDV and BDV-related polypeptide p10 herein.

Testkits for the detection of a BDV can be used in the conventional method. More specifically, a sample is prepared from an animal that is to be tested for a BDV. The sample is tested as to whether it contains an antibody to a BDV. Once prepared, the sample is contacted with the testkit such that the protein of the testkit will bind to antibodies against a BDV located in the sample. Once the sample is contacted, the sample is compared to a benchmark sample that does not contain any antibodies that bind with a BDV. If the sample matches the benchmark sample, then the animal being tested does not have a BDV. However, if the sample does not match the benchmark sample, then the animal being tested has a BDV.

A further aspect of this invention teaches the use of BDV polypeptide p10 to raise a BDV-specific immune response in animals as demonstrated in Example 3. As known in prior art the raising of a specific immune response provides protection, therefore, a vaccine, against the virus infection. Both p10 protein, peptides, polypeptides and the nucleic acid fragments that encodes polypeptide p10 and its fragments may be used as vaccines against BDV and BDV-related viruses. The use of proteins, peptides and polypeptides as vaccines has been known for a long time, but recently, it has been taught that nucleic acid fragments in the form of DNA in an expression vector, or in the form of DNA or RNA in an infectious suicide virus particle, also can be used as vaccines (Tang, Nature 356:152 (1992); Ulmer, Science 259:1745 (1993)). These nucleic acid vaccines can be delivered intramuscularly by injection or intradermally by a device, preferably a gene-gun. At the site of vaccination, the inoculated nucleic acid fragments are expressed transiently as proteins, peptides or polypeptides to raise specific immune responses and provide protection.

Example 1

Cloning of BDV ORFx1 Into Prokaryotic Expression Vector and its Expression as p10 Recombinant Protein.

Total RNA was isolated from the BDV-infected MDCK cells (ATCC CCL-34 for MDCK cells) by standard techniques "Molecular Cloning—A Laboratory Manual" Second Edition by J. Sambrook, E. F. Fritsch and T. Mariatis, Cold Spring Harbor Laboratory Press 1989 and Malik et al., Virology 258:65–72 (1999); see also Briese et al., Proc. Natl. Acad. Sci. 91:4362–4366 (1994); Briese et al., J. Clin. Mirobiol. 33:348–351 (1995); de la Torre et al., Virus Research 44:3344 (1996); Pyper et al., Virology 195:229–238 (1993); Schneemann et al., Virology 210:1–8 (1995); Schneider et al., J. Virol. 68:5007–5012 (1994); Schwemmle et al., J. Biol. Chem. 273:9007–9012 (1998); Wehner et al., J. Gen. Virol. 78:2459–2466 (1997); Woude et al., Science 250:1278–1281 (1990); Cubitt et al., J. Virol. 68:1382–1396 (1994); U.S. Pat. No. 5,654,401 to Clements et al., issued Aug. 5, 1997; U.S. Pat. No. 5,854,417 to Clements et al., issued Dec. 29, 1998; WO 98/30238 to De la Torre, published Jul. 16, 1998; WO 96/21020 to Lipkin et al., published Jul. 11, 1996; EP 0791654A1 to Richt, published Aug. 27, 1997). The BDV ORFx1 cDNA was amplified from 2 microgram of total RNA by use of (SEQ ID NO:1 and SEQ ID NO: 2, respectively)

primer 1=5'-TGT GAATTCAATGAGTTCCGACCTCCGG-3', (SEQ ID NO:1) and
    primer 2=5'-TGC CTCGAGTCATTCGATAGCTGCTCCC-3' (SEQ ID NO:2)

in RT-PCR. Thirty cycles, each consisted of denaturation at 94° C. for 2 mins, annealing at 54° C. for 1 min and extension at 72° C. for 7 mins, followed by a final extension at 72° C. for 10 mins were performed. The amplified product was purified from agarose gels, digested with EcoRI and XhoI, and cloned into the EcoRI-XhoI sites of the pGEX4T-3 vector (Pharmacia, Catalog number 27-4583-01) in-frame and downstream of the glutathione-S-transferase (GST) gene of Schistosoma japonicum controlled by the tac promoter. This resultant construct pGEX-ORFx1 was used to transform competent E. coli bacteria, strain JM109, grown to log phase. As control, JM109 bacteria transformed by the pGEX4T-3 vector were grown the same way. Test and control bacteria were induced by IPTG (0.1 mM) for 2.5 hours to ensure high-level expression of the fusion protein. The bacteria were then spun down and re-suspended in buffer (1×PBS, 1% triton-X100). Two cycles of freeze-thaw were followed by 6 cycles of sonication on ice, each at a 15 second burst to disrupt the cells. The membrane and soluble fractions were separated by high speed centrifugation at 12,000×g for 1 hour. The soluble cell-free fractions from the test and control bacterial cultures were recovered after centrifugation. The GST-p10 fusion protein from the test preparation and the GST protein from the control preparation were affinity purified by passing the soluble cell free fraction from each through a matrix containing glutathione (Glutathione Sepharose 4B; Pharmacia, catalog number 27-4570-01) according to the manufacturer's instruction. The eluted GST-p10 fusion protein and the control GST protein were analyzed by western blot against a serum from a rabbit infected with BDV (FIG. 1). As shown in FIG. 1, the purified GST-p10 fusion protein reacted with the infected serum. In contrast, the GST control protein not containing the p10 moiety did not react with the antiserum. Sequencing to determine the nucleotide sequence of the EcoRI-XhoI DNA fragment in the pGEX-ORFx1 vector that encode the p10 moiety of the GST-p10 fusion protein was performed by standard method (Sanger, supra). Computer analysis of this nucleotide sequence to give the amino acid sequence of the ORFx1 was performed by use of the PCgene software (Intellegenetic Suite, CA). This amino acid sequence (not underlined segment) is given as SEQ ID NO: 6 in FIG. 3.

Example 2

Cloning of BDV ORFx1 Into Eukaryotic Expression Vector

Total RNA was isolated from the BDV-infected MDCK cells by standard techniques ("Molecular Cloning—A Laboratory Manual" Second Edition by J. Sambrook, E. F. Fritsch and T. Mariatis, Cold Spring Harbor Laboratory Press 1989). The BDV ORFx1 cDNA was amplified by RT-PCR from 2 microgram of total RNA by use of (SEQ ID NO:3 and SEQ ID NO: 4, respectively)

Primer 5'-CGG GAATTCACCATGGGTTCCGACCTCCGG-3', (SEQ ID NO:3) and
    Primer 5'-TGC CTCGAGTCACTTGTCATCGTCGTCCTTGTAGT CTTCGATAGCTGCTCCC-3' (SEQ ID NO:4)

which also contained the DNA sequence (Bold) coding for a synthetic marker called FLAG. Thirty cycles, each consisted of denaturation at 94° C. for 2 mins, annealing at 54° C. for 1 min and extension at 72° C. for 2 mins, followed by a final extension at 72° C. for 10 mins were performed. The amplified product was purified from agarose gels, digested with EcoRI and XhoI, and cloned into the EcoRI-XhoI sites of the pcDNA-3 eukaryotic expression vector (Invitrogen, Catalog number V790-20) to give the new construct pcORFx1-FLAG. Sequencing to determine the nucleotide sequence of the EcoRI-XhoI DNA fragment in the pcORFx1-FLAG vector was performed by standard methods (Sanger, supra). This nucleotide sequence of ORFx1-FLAG (SEQ ID NO:5; FIG. 2) has been submitted to the GeneBank (Accession Number: 030353). Computer analysis of this nucleotide sequence to give the amino acid sequence of the ORFx1-FLAG (SEQ ID NO:6; FIG. 3) was performed by use of the PCgene software (Intellegenetic Suite, CA). The FLAG amino acids are underlined. The ORFx1 amino acids are not underlined.

Example 3

Figure 6:
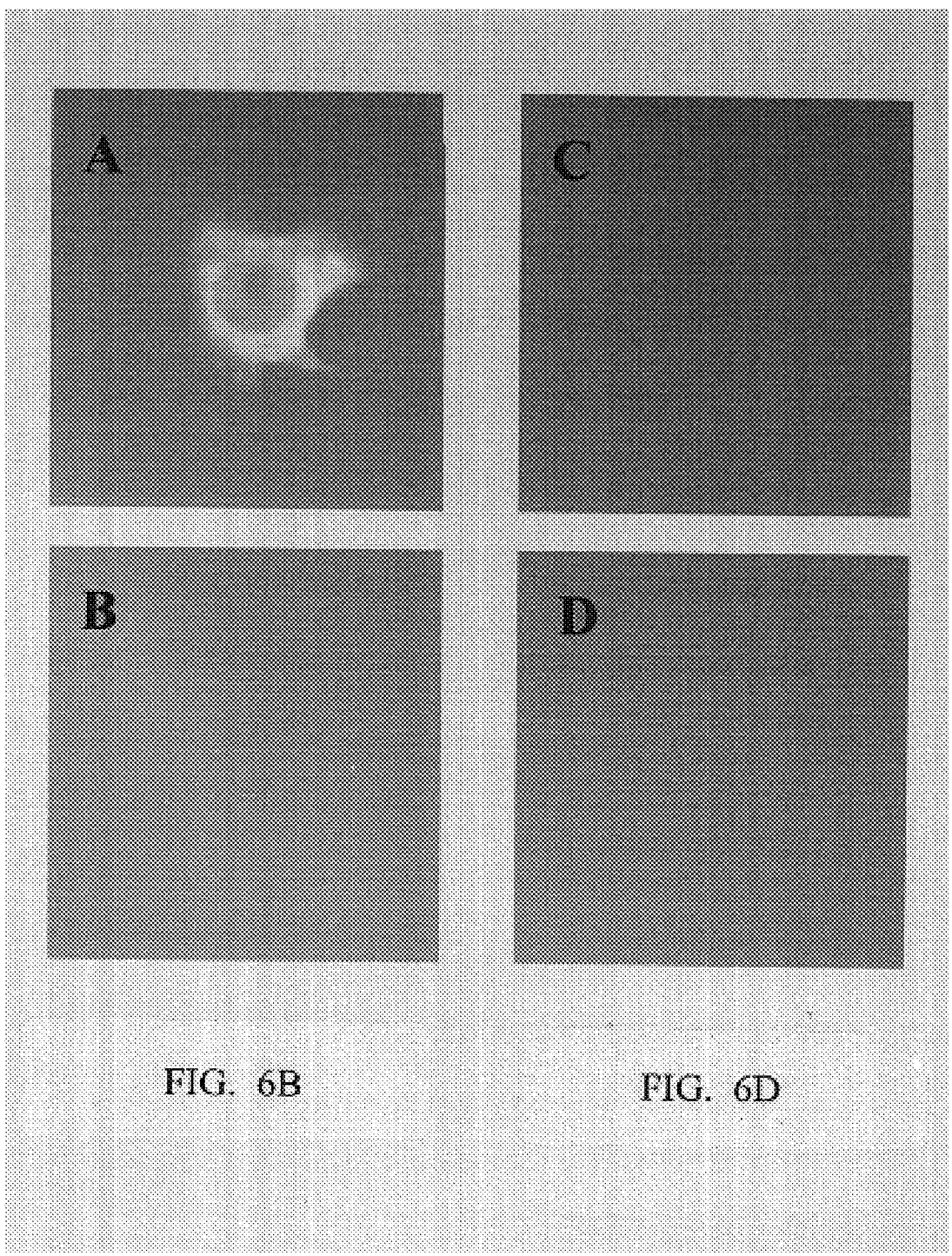
FIG. 6A, FIG. 6B, FIG. 6C and FIG. 6D depict the specificity of the anti-BDV polypeptide p10 rabbit antiserum to cells expressing BDV polypeptide p10. The primate cells COS-7 (ATCC accession number CRL-1651) were transfected with the eukaryotic expression vector pORFx1-FLAG created as described in Example 2. The transfected cells expressing BDV polypeptide p10 (FIG. 6A and FIG. 6C) and the non-transfected cells (FIG. 6B and FIG. 6D) were stained in immunofluorescence assays (IFA) by the anti-BDV polypeptide p10 rabbit serum (panels A and B) prepared as described in Example 3, and previously tested as shown in FIG. 4. Only the transfected cells expressing BDV polypeptide p10 were stained (FIG. 6A). The preimmune serum did not stain the transfected (FIG. 6C) or the non-transfected (FIG. 6D) cells.

Specific Antiserum to Recombinant p10 and its Use to Detect BDV Infection in Tissue Cultured Cells The GST-p10 fusion protein from the pGEX-ORFx1-transformed JM109 E. coli bacteria was purified by affinity chromatography as described in Example 1 and dialyzed against PBS for 16 hours at 4° C. The concentration of the GST-p10 fusion protein in solution after dialysis was determined by use of a spectrophotometer. Monospecific polyvalent antiserum to the GST-p10 fusion protein was generated by subcutaneous immunization of a rabbit with 1 mg of the GST-p10 fusion protein in complete Freund's adjuvant (CFA). Four and eight weeks later, this rabbit received booster immunizations with the same quantity of the GST-p10 fusion protein. Ten days after the last booster injection, the rabbit was bled and the serum was tested against BDV-infected cells and non-infected cells (FIG. 4 and FIG. 5), and cells expressing p10 (FIG. 6) after transfection of the pcORFx1-FLAG eukaryotic expression vector constructed in Example 2. FIG. 4 shows that in Western blot, the rabbit antiserum reacted with the infected C6BV cells and not the non-infected C6 cells. Likewise, FIG. 5 shows the rabbit antiserum positively stained the infected MDCK/BV cells in IFA, but did not stain the non-infected MDCK cells. Thus, the rabbit antiserum was able to detect BDV infection in tissue cultured cells. FIG. 6 shows that cells transfected with the pcORFx1-FLAG construct expressed the BDV p10 which was detected by the rabbit antiserum in IFA. In contrast, cells not transfected, although expressing cellular proteins and not the BDV p10, were not reactive to the rabbit antiserum in IFA.

Example 4

Figure 7:
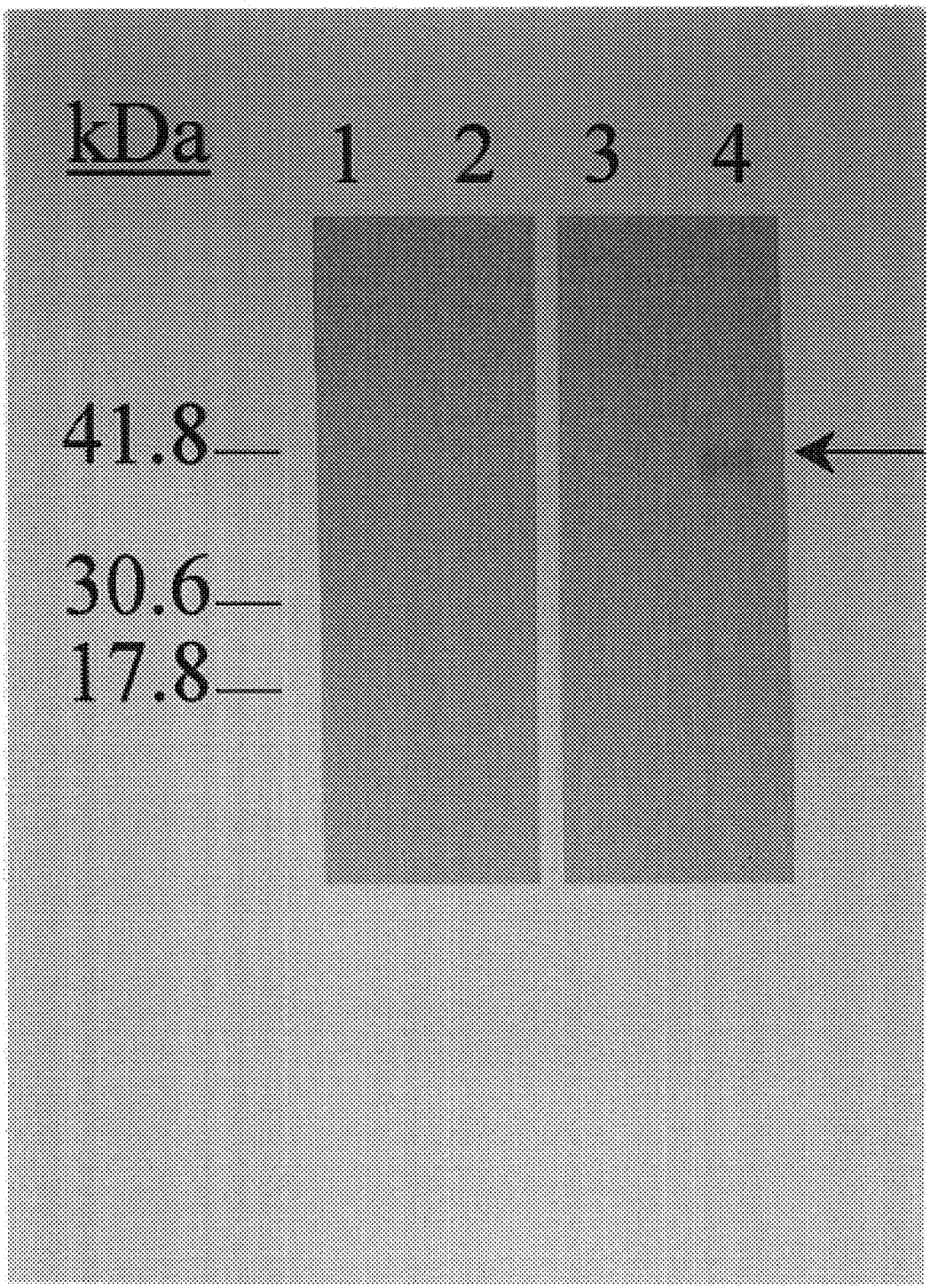
FIG. 7 depicts the detection of anti-BDV polypeptide p10 antibodies in serum from a BDV-infected rabbit. Affinity column-purified GST protein (lanes 1 and 2) and GST-BDV polypeptide p10 fusion protein (lanes 3 and 4) were used as antigen substrates in western blot to test for antigen-specific antibodies in serum from a rabbit experimentally infected (lanes 2 and 4) and not infected (lanes 1 and 3) with BDV.
Figure 8:
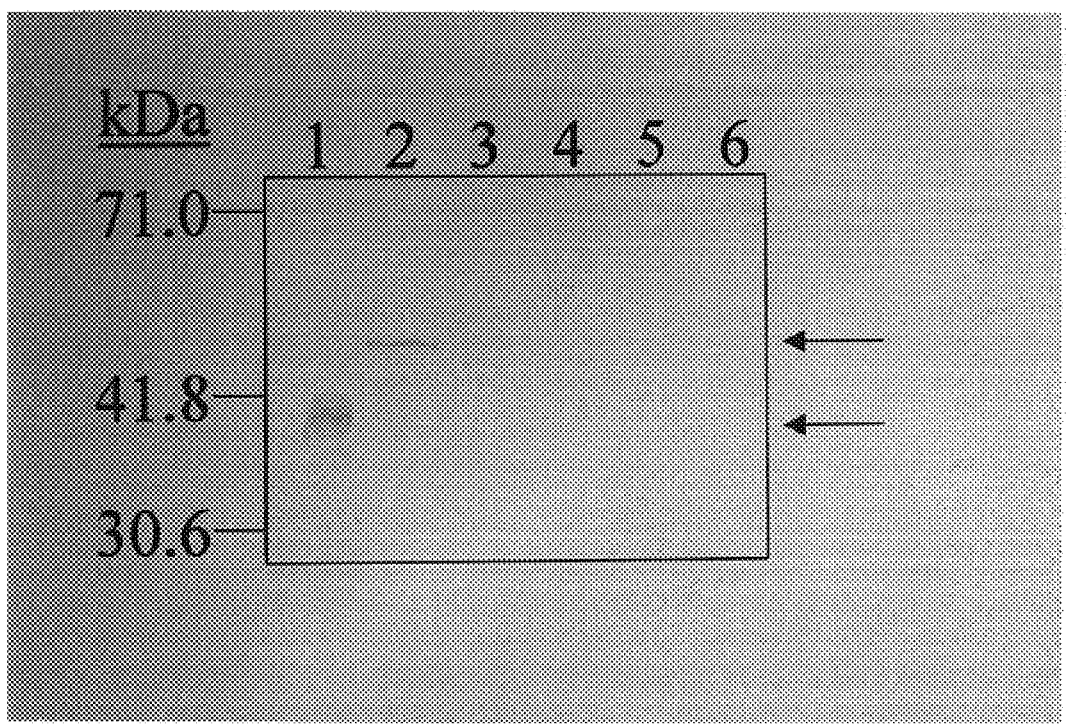
FIG. 8 depicts the detection of anti-BDV antibodies in serum from a BDV-infected horse. Affinity column-purified GST protein (lanes 3 and 6), GST-BDV polypeptide p10 fusion protein (lanes 1 and 4) and GST-BDV p24 fusion protein (lanes 2 and 5) were used as antigen substrates in western blot to test for antigen-specific antibodies in sera from horses naturally infected (lanes 1, 2 and 3) and not infected (lanes 4, 5 and 6) with BDV. The GST-BDV polypeptide p10 fusion protein detected anti-BDV polypeptide p10 specific antibodies in serum of the infected horse. Construction of the plasmid expressing the GST-BDV p24 BDV protein has previously been described, and detection of antibodies specific to this protein suggested BDV infection of the horse (Kishi et al. FEBS Lett. 364:293–297 (1995).

Recombinant p10 Linked to Solid Support Detects Infection by BDV or BDV-associated Viruses The GST-p10 fusion protein and the GST protein from *E. coli* bacteria transformed by the pGEX-ORFx1 and the pGEX4T-3 plasmid, respectively, were affinity purified by passing the soluble cell free fraction from each through a matrix containing glutathione (Glutathione Sepharose 4B; Pharmacia, Catalog number 27-4570-01) according to the manufacturer's instruction as described in Example 1. The eluted GST-p10 fusion protein and the control GST protein were suspended in Laemmli sample buffer (Laemmli, Nature 227:680 (1970)), heated at 100° C. for 2 min, and resolved by sodium dodecyl sulfate-polyacrylamide gel electrophoresis (SDS-PAGE) on 12% polyacrylamide gel. The resolved proteins on the gel were transferred to a nitrocellulose membrane by electroblotting. The nitrocellulose membrane providing solid support to the proteins was cut into strips, and each strip was soaked in a solution containing 5% (w/v) powdered skimmed milk at room temperature overnight. The nitrocellular strips were then allowed to react with serum collected from a BDV-infected rabbit. As controls, the replicates of the strips were allowed to react with a serum collected from the same rabbit before infection by BDV. Serial dilutions of the sera from the infected rabbit and from the non-infected control were tested by incubation at room temperature for 2 hrs with the nitrocellular strips containing the respective proteins. Each strip was then washed three times with washing buffer (PBS with 0.5%(v/v) Tween-20), and incubated with 200 ng/ml Protein A|G marked with alkaline phosphatase (Pierce, Rockford, Ill.; Product number 32391). After washing three times with washing buffer, the strips were developed in 1× solution of Substrate (Alkaline Phosphatase Conjugate Substrate Kit; Catalog number 170-6432, Bio-Rad Laboratories, Hercules, Calif.). FIG. 7 shows that only the serum from the infected rabbit gave a positive band against the recombinant BDV p10, serum from non-infected rabbit did not. Likewise, horse sera tested against the immunoblotted recombinant BDV p10 gave comparable results, i.e., serum from an infected horse gave a positive band against the recombinant BDV p10, whereas sera from non-infected horses did not (FIG. 8).

Example 5

Nuclear Localization of Polypeptide p10 and Interaction of Polypeptide p10 With p40

This example establishes that polypeptide p10 localizes in the cytoplasm and nucleus and interacts with polypeptide p40.

General Materials and Methods

Cell Lines and Antibodies

The MDCK/BV cell line was as discussed in the preceding examples. Rat glial tumor cells not infected with BDV (Cell line C6) and persistently infected with BDV (Cell line C6BV) (ATCC CCL-107), and cos-7 cells (ATCC CRL-1651) were also used. Cells were cultured in Dulbecco's modified Eagle's medium with 10% fetal bovine serum, 2 mM glutamine, 100 U/ml penicillin and 100 micrograms/ml streptomycin (Malik et al., Virology 258:65–72 (1999)). Antibodies that bind with polypeptide p10 or polypeptide p40 were made as described in Example 3 and the literature (Malik et al., Virology 258:65–72 (1999)).

Expression Vectors

Prokaryotic and eukaryotic expression vectors for polypeptide p10 and polypeptide p40 were made as described in the literature (Malik et al., Virology 258:65–72 (1999)). Briefly, total RNA was isolated from MDCK/BV cells. cDNA molecules encoding polypeptide p10 were made using specific primer pairs and RT-PCR. The cDNA molecule was digested with EcoRI and XhoI and cloned in-frame to the GST sequence in the pGEX 4T-3 vector (Pharmacia) to provide pGEX-ORFx1 prokaryotic expression vector. cDNA molecules encoding polypeptide p40 were made using specific primer pairs and RT-PCR The cDNA molecules were cloned into the BamH1 site of pGEX-5X-3 vector (Pharmacia) to provide pGEX-N.WILD construct. Eukaryotic expression vectors for polypeptide p10 (pcORFx1-FLAG) was made using RT-PCR with ORFx1 specific primers, one of which included a sequence encoding the FLAG epitope tag. The ORFx-1-FLAG fragment (GenBank accession number 030353) was cloned into the EcoRI-XhoI site of the pcDNA3 vector (InVitrogen). The construction of the eukaryotic expression vector pDL-N.WILD for p40 as described in Kobayashi et al., Virology 243:188–197 (1998).

Eukaryotic Expression

Expression of polypeptide p10 and polypeptide p40 in eukaryotic cells was performed as described in the literature (Malik et al., Virology 258:65–72 (1999)). Briefly, untransfected cells were transfected with plasmid using Lipfectamine from Life Technologies. Cells were fixed between about 24 hours and about 48 hours after transfection with 4% parafomaldehyde and stained with the appropriate antibody. Cells not transfected or mock-transfected were treated the same way and were used as controls. Immunofluorescence was detected suing epifluroescence microscopy or a confocal laser scanning microscope using a krypton and/or argon lamp.

Immunoprecipitation

Immunoprecipitation of polypeptide p10 and polypeptide p40 was performed as described in the literature (Malik et al., Virology 258:65–72 (1999)). Briefly, transfected or persistently infected cells were lysed by freeze-thaw and centrifuged. The soluble fraction was reacted with anti-p10 antiserum and the precipitate recovered by incubation with protein G beads. Protein bound to the beads was recovered and resolved by SDS-PAGE and Western blotting.

Protein-protein Interactions

Protein-protein interactions between polypeptide p10 and polypeptide p40 were evaluated as described in the literature (Malik et al., Virology 258:65–72 (1999)). Briefly, in vitro transcription/translation of pcORFx1-FLAG was performed by use of the TNT-coupled rabbit reticulocyte lysate system (Promega). A sample of the in vitro products was resolved by denaturing SDS-PAGE and analyzed after fluorography, or immunoprecipitation by use of anti-FLAG monoclonal antibody before SDS-PAGE and fluorography. The GST-p40 fusion protein was purified by glutathione column chromatography of the lysate from the pGEX-N.WILD-transformed bacteria. The purified protein was cross-linked to glutathione 4B beads to provide a solid phase. For protein-protein interaction, between about 1 and about 2 micrograms of GST-p40 was then mixed with the 35S-labeled in vitro transcribed/translated p10-FLAG protein. After washing, proteins bound to the beads were resolved by SDS-PAGE and analyzed by Western blotting with appropriate antibodies. In addition, the blot was subjected to autoradiography to detect any bound 35S-labeled proteins.

Nuclear Localization of Polypeptide p10 in BDV-infected Cells

Figures 9A, 9B, 9C, 9D:
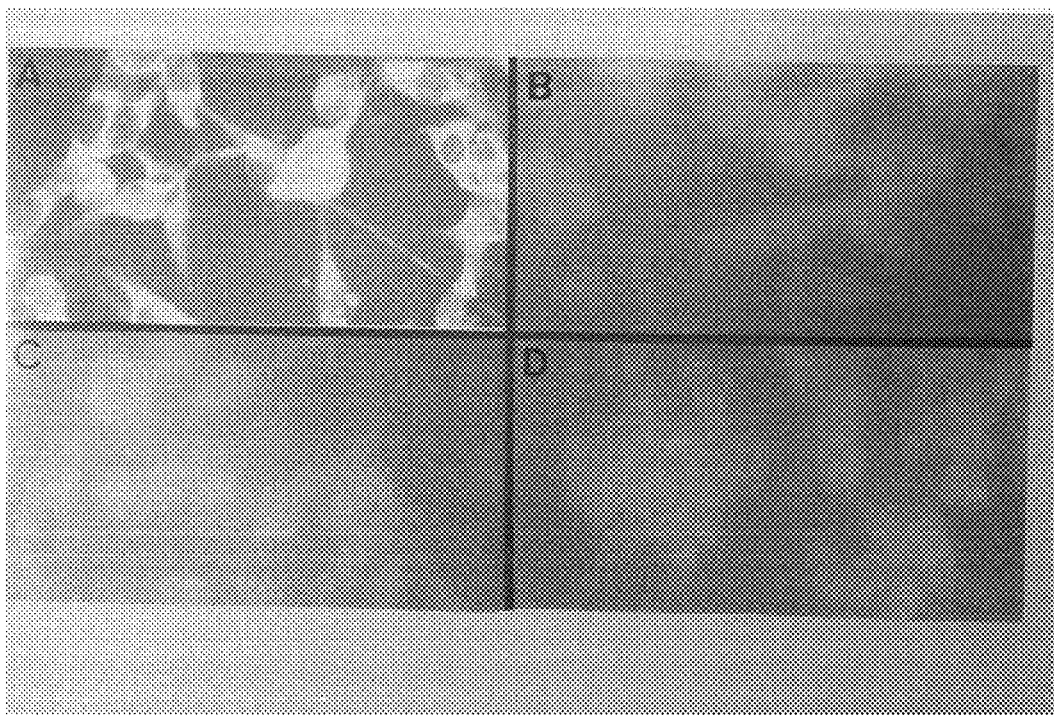
FIG. 9 depicts the subcellular localization of polypeptide p10 in BDV-infected cells. Antiserum specific for polypeptide p10 was used to stain C6BV (FIG. 9A) and C6 (FIG. 9B) cells via IFA. C6BV (FIG. 9C) and C6 (FIG. 9D) cells were also stained with prebleed serum as a control. The FITC-conjugated protein A was used as a second antibody. The stained cells were examined using an epifluroescence microscope at 160× magnification. The staining was observed in the nucleus and in the cytoplasm of the infected cells.

As shown in FIG. 9, the subcellular localization of polypeptide p10 was investigated using rabbit anti-p10 antibodies in BDV-infected C6BV cells and noninfected C6 cells by indirect immunofluorescence. As shown in FIG. 9A, the anti-p10 staining was localized in the cytoplasm and nucleus of the C6BV cells. The C6 cells were not stained (FIG. 9B). Both C6BV and C6 cells were not stained by the preimmune sera (FIG. 9C and FIG. 9D).

In Vivo Interaction of Polypeptide p10 and Polypeptide p40

Soluble cell lysate from C6BV cells was immunoprecipitated with anti-p10 serum and the precipitate recovered by protein G beads. Analysis of the immune precipitate with a BDV-infected rabbit serum showed that three proteins, p10, p40 and p24, were coprecipitated by the anti-p10 serum. Preimmune serum did not immunoprecipitate proteins from the soluble cell lysates of C6BV. The analysis was performed using Western blotting and protein A cross-linked to alkaline phosphatase reactive with BCIP/NBT to detect antibody-antigen interactions.

Eukaryotic expression vectors pcORFx1-FLAG and pDL-N.WILD were cotransfected into Cos-7 cells. The Cos-7 cells were used because they allow plasmid replication of the pcORFx1-FLAG, which contains the SV40 origin of replication, and thereby provide increased expression of p10. Soluble cell lysate from the cotransfected Cos-7 cells was immunoprecipitated with anti-p10 serum and the precipitate recovered by protein G beads. Analysis of the immune precipitate via western blotting with a BDV-infected rabbit serum showed that p10 and p40 were coprecipitated by the anti-p10 serum. Preimmune serum did not immunoprecipitate p10 and/or p40. Western blots were developed using Protein A cross-linked to alkaline phosphatase reactive to BCIP/NBT to detect antibody-antigen interactions.

Cos-7 cells were cotransfected with pcORFx1-FLAG and pDL-N.WILD plasmids, both plasmids containing an SV40 origin and the product reacted with anti-p10 serum. The cytoplasm of Cos-7 cells transfected with the pcORFx1-FLAG plasmid alone were stained by the anti-p10 serum. Although p10 is a small polypeptide, it was not observed to diffuse into the nucleus of singularly transfected cells. Cos-7 cells cotransfected with the pcORFx1-FLAG and the pDL-N.WILD plasmid stained with a rabbit anti-p10 antibody or a mouse anti-p40 serum gave nuclear staining. Two-tone staining using the p10 and p40 specific sera revealed the two viral proteins colocalized in the nucleus of the cotransfected cells. As controls, Cos-7 transfected with the p40-expressing pDL-N.WILD plasmid alone gave nuclear staining. No staining was observed with the nontransfected Cos-7 cells.

In Vitro Confirmation of p10–p40 Interaction

The pcORFx1-FLAG vector was in vitro transcribed by the T7 polymerase and translated to give the $^{35}$S-labeled p10-FLAG, which could be immunoprecipitated with the anti-FLAG monoclonal antibody. The GST-p40 fusion protein from pGEX-N.WILD-transformed bacteria was cross-linked to glutathione 4B beads. The labeled p10-FLAG protein was allowed to interact with the GST-p40 bound to solid phase. Analysis of the bound proteins via Western blotting showed that the labeled p10-FLAG protein had bound to the GST-p40 protein, establishing that the p10 had interacted with the p40.

CONCLUSION

While various embodiments of the present invention have been described above, it should be understood that they have been presented by the way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined in accordance with the following claims and their equivalents.

All publications, including patent documents and scientific articles, referred to in this application are incorporated by reference in their entirety for all purposes to the same extent as if each individual publication were individually incorporated by reference. All headings are for the convenience of the reader and should not be used to limit the meaning of the text that follows the heading, unless so specified.

What is claimed is:

1. A polypeptide encoded by:
   the nucleic acid sequence of SEQ ID NO:5 or SEQ ID NO:7;
   wherein said polypeptide comprises at least one bioactivity of a p10 polypeptide of Borna Disease Virus.

2. A polypeptide of claim 1 that binds with an antibody that binds with a p10 polypeptide of Borna Disease Virus.

3. A fusion protein comprising the polypeptide of claim 1.

4. A nucleic acid molecule encoding a polypeptide of claim 1.

5. The nucleic acid molecule of claim 4 operably linked to a control sequence.

6. The nucleic acid molecule of claim 4 in a vector.

7. The nucleic acid molecule of claim 4 in a cell that does not normally express said nucleic acid molecule.

8. A test kit for detecting a specific binding member for a Borna Disease Virus, said test kit comprising the polypeptide of claim 1.

9. A test kit for detecting a Borna Disease Virus nucleic acid molecule, said test kit comprising the nucleic acid molecule of claim 4.

10. A polypeptide comprising:
    the amino acid sequence of SEQ ID NO:6 or SEQ ID NO:8.

11. A nucleic acid molecule encoding the polypeptide of claim 10.

* * * * *

SEQUENCE LISTING

<160> NUMBER OF SEQ ID NOS: 20

<210> SEQ ID NO 1
<211> LENGTH: 28
<212> TYPE: DNA
<213> ORGANISM: Borna disease virus -continued

```
<400> SEQUENCE: 1
tgtgaattca atgagttccg acctccgg                                          28

<210> SEQ ID NO 2
<211> LENGTH: 28
<212> TYPE: DNA
<213> ORGANISM: Borna disease virus

<400> SEQUENCE: 2
tgcctcgagt cattcgatag ctgctccc                                          28

<210> SEQ ID NO 3
<211> LENGTH: 30
<212> TYPE: DNA
<213> ORGANISM: Borna disease virus

<400> SEQUENCE: 3
cgggaattca ccatgggttc cgacctccgg                                        30

<210> SEQ ID NO 4
<211> LENGTH: 52
<212> TYPE: DNA
<213> ORGANISM: Borna disease virus

<400> SEQUENCE: 4
tgcctcgagt cacttgtcat cgtcgtcctt gtagtcttcg atagctgctc cc               52

<210> SEQ ID NO 5
<211> LENGTH: 285
<212> TYPE: DNA
<213> ORGANISM: Borna disease virus

<400> SEQUENCE: 5
atgggttccg acctccggct gacattgctt gaactagtca ggaggctcaa tggcaacgcg       60
accatcgagt ctggtcgact ccctggagga cgaagaagat ccccagacac tacgacggga      120
acgatcgggg tcaccaagac cacgaagat cccaaggaat gcattgaccc aaccagtcga       180
ccagctcctg aaggacctca ggaagaaccc ctccatgatc tcagacccag accagcgaac      240
cggaagggag cagctatcga agactacaag gacgacgatg acaag                      285

<210> SEQ ID NO 6
<211> LENGTH: 95
<212> TYPE: PRT
<213> ORGANISM: Borna disease virus

<400> SEQUENCE: 6

Met Gly Ser Asp Leu Arg Leu Thr Leu Leu Glu Leu Val Arg Arg Leu
1               5                   10                  15

Asn Gly Asn Ala Thr Ile Glu Ser Gly Arg Leu Pro Gly Gly Arg Arg
            20                  25                  30

Arg Ser Pro Asp Thr Thr Thr Gly Thr Ile Gly Val Thr Lys Thr Thr
        35                  40                  45

Glu Asp Pro Lys Glu Cys Ile Asp Pro Thr Ser Arg Pro Ala Pro Glu
    50                  55                  60

Gly Pro Gln Glu Glu Pro Leu His Asp Leu Arg Pro Arg Pro Ala Asn
65                  70                  75                  80

Arg Lys Gly Ala Ala Ile Glu Asp Tyr Lys Asp Asp Asp Asp Lys
                85                  90                  95
```

```
<210> SEQ ID NO 7
<211> LENGTH: 261
<212> TYPE: DNA
<213> ORGANISM: Borna disease virus

<400> SEQUENCE: 7
atgggttccg acctccggct gacattgctt gaactagtca ggaggctcaa tggcaacgcg      60
accatcgagt ctggtcgact ccctggagga cgaagaagat ccccagacac tacgacggga     120
acgatcgggg tcaccaagac cacggaagat cccaaggaat gcattgaccc aaccagtcga     180
ccagctcctg aaggacctca ggaagaaccc ctccatgatc tcagacccag accagcgaac     240
cggaagggag cagctatcga a                                                261

<210> SEQ ID NO 8
<211> LENGTH: 87
<212> TYPE: PRT
<213> ORGANISM: Borna disease virus

<400> SEQUENCE: 8

Met Gly Ser Asp Leu Arg Leu Thr Leu Leu Glu Leu Val Arg Arg Leu
  1               5                  10                  15

Asn Gly Asn Ala Thr Ile Glu Ser Gly Arg Leu Pro Gly Gly Arg Arg
             20                  25                  30

Arg Ser Pro Asp Thr Thr Thr Gly Thr Ile Gly Val Thr Lys Thr Thr
         35                  40                  45

Glu Asp Pro Lys Glu Cys Ile Asp Pro Thr Ser Arg Pro Ala Pro Glu
     50                  55                  60

Gly Pro Gln Glu Glu Pro Leu His Asp Leu Arg Pro Arg Pro Ala Asn
 65                  70                  75                  80

Arg Lys Gly Ala Ala Ile Glu
                 85

<210> SEQ ID NO 9
<211> LENGTH: 257
<212> TYPE: DNA
<213> ORGANISM: Borna disease virus

<400> SEQUENCE: 9
gttccgacct ccggctgaca ttgcttgaat tagtcaggag gctcaatggc aacgggacca      60
tcgagtctgg tcgactccct ggaggacgaa gaagatcccc agacactacg acggaaacga     120 tcgggtcac caagaccacg gaagatccca aggaatgcat tgacccaacc ggtagaccag      180
ctcctgaagg acctcaggaa gaaccctcc atgatctcag acccagacca gcgaaccgga      240
agggagcagc tatcgaa                                                     257

<210> SEQ ID NO 10
<211> LENGTH: 257
<212> TYPE: DNA
<213> ORGANISM: Borna disease virus

<400> SEQUENCE: 10
gttccgacct ccggctgaca ttgcttgaat tagtcaggag gctcaatggc aacgcgacca      60
tcgagtctgg tcgactccct ggaggacgaa gaagatcccc agacactacg acggaacgg      120 tcgggtcac caagaccacg gaagatccca aggaatgcat tgacccaacc ggtagaccag      180
ctcctgaagg acctcaggaa gaaccctcc atgatctcag acccagacca gcgaaccgga      240
agggagcagc tatcgaa                                                     257
```

```
<210> SEQ ID NO 11
<211> LENGTH: 257
<212> TYPE: DNA
<213> ORGANISM: Borna disease virus

<400> SEQUENCE: 11
gttccgacct ccggctgaca ttgcttgaat tagtcaggag gctcaatggc aacgcgacca      60
tcgagtctgg tcgactccct ggaggacgaa gaagatcccc agacactacg acgggaacgg     120
tcggggtcac caagaccacg gaagatccca aggaatgcat tgaccaacc ggtagaccag      180
ctcctgaagg acctcaggaa gaacccctcc atgatctcag acccagacca gcgaaccgga    240
agggagcagc tatcgaa                                                    257

<210> SEQ ID NO 12
<211> LENGTH: 255
<212> TYPE: DNA
<213> ORGANISM: Borna disease virus

<400> SEQUENCE: 12
tccgacctcc ggctgacatt gcttgaacta gtcaggaggc tcaatggcaa cgcgaccatc      60
gagtctggtc gactccctgg aggacgaaga agatccccag acactacgac gggaacgacc     120
ggggtcacca agaccacgga aggtcccaag gaatgcattg acccaaccag tagaccagct    180
cctgaaggac ctcaggaaga accctccat gatctcagac cagaccagc gaaccggaag     240
ggagcagctg tcgaa                                                      255

<210> SEQ ID NO 13
<211> LENGTH: 255
<212> TYPE: DNA
<213> ORGANISM: Borna disease virus

<400> SEQUENCE: 13
tccgacctcc ggctgacatt gcttgaatta gtcaggaggc tcaatggcaa cgcgaccatc      60
gagtctggtc gactccctgg aggacgaaga agatccccag acactacgac ggaaacgatc    120
ggggtcacca agaccacgga agatcccaag gaatgcattg acccaaccgg tagaccagct    180
cctgaaggac ctcaggaaga accctccat gatctcagac cagaccagc gaaccggaag     240
ggagcagcta tcgaa                                                      255

<210> SEQ ID NO 14
<211> LENGTH: 221
<212> TYPE: DNA
<213> ORGANISM: Borna disease virus

<400> SEQUENCE: 14
ggaggctcaa tggcaacgcg accatcgagt ctggtcgact ccctggagga cgaagaagat      60
ccccagacac tacgacggga cgatcgggg tcaccaagac cacggaagat cccaaggaat     120
gcattgaccc aaccagtaga ccagctcctg aaggacctca ggaagaaccc ctccacgatc    180
tcagacccag accagcgaac cggaagggag cagctgtcga a                         221

<210> SEQ ID NO 15
<211> LENGTH: 87
<212> TYPE: PRT
<213> ORGANISM: Borna disease virus

<400> SEQUENCE: 15

Met Ser Ser Asp Leu Arg Leu Thr Leu Leu Glu Leu Val Arg Arg Leu
```

```
                1               5                    10                   15
Asn Gly Asn Ala Thr Ile Glu Ser Gly Arg Leu Pro Gly Gly Arg Arg
                    20                  25                  30

Arg Ser Pro Asp Thr Thr Thr Gly Thr Val Gly Val Thr Lys Thr Thr
            35                  40                  45

Glu Asp Pro Lys Glu Cys Ile Asp Pro Thr Gly Arg Pro Ala Pro Glu
        50                  55                  60

Gly Pro Gln Glu Glu Pro Leu His Asp Leu Arg Pro Arg Pro Ala Asn
65                  70                  75                  80

Arg Lys Gly Ala Ala Ile Glu
                85

<210> SEQ ID NO 16
<211> LENGTH: 82
<212> TYPE: PRT
<213> ORGANISM: Borna disease virus

<400> SEQUENCE: 16

Met Ser Ser Asp Leu Arg Leu Thr Leu Leu Glu Leu Val Arg Arg Leu
1               5                   10                  15

Asn Gly Asn Ala Thr Ile Glu Ser Gly Arg Leu Pro Gly Gly Arg Arg
                    20                  25                  30

Arg Ser Pro Asp Thr Thr Thr Gly Thr Val Gly Val Thr Lys Thr Thr
            35                  40                  45

Glu Asp Pro Lys Glu Cys Ile Asp Pro Thr Gly Arg Pro Ala Pro Glu
        50                  55                  60

Gly Pro Gln Glu Glu Pro Leu His Asp Leu Arg Pro Arg Pro Ala Asn
65                  70                  75                  80

Arg Lys

<210> SEQ ID NO 17
<211> LENGTH: 63
<212> TYPE: PRT
<213> ORGANISM: Borna disease virus

<400> SEQUENCE: 17

Met Ser Ser Asp Leu Arg Leu Thr Leu Leu Gly Leu Val Arg Arg Leu
1               5                   10                  15

Asn Gly Asn Gly Thr Ile Glu Ser Gly Arg Leu Pro Gly Gly Arg Arg
                    20                  25                  30

Arg Ser Pro Asp Thr Thr Thr Gly Thr Ile Gly Val Thr Lys Thr Thr
            35                  40                  45

Glu Asp Pro Lys Glu Cys Ile Asp Pro Thr Gly Arg Pro Ala Pro
        50                  55                  60

<210> SEQ ID NO 18
<211> LENGTH: 63
<212> TYPE: PRT
<213> ORGANISM: Borna disease virus

<400> SEQUENCE: 18

Met Ser Ser Asp Leu Arg Leu Thr Leu Leu Gly Leu Val Arg Arg Leu
1               5                   10                  15

Asn Gly Asn Gly Thr Ile Glu Ser Gly Arg Leu Pro Gly Gly Arg Arg
                    20                  25                  30

Arg Ser Pro Asp Thr Thr Thr Gly Thr Ile Gly Val Thr Lys Thr Thr
            35                  40                  45
```

```
<210> SEQ ID NO 19
<211> LENGTH: 63
<212> TYPE: PRT
<213> ORGANISM: Borna disease virus

<400> SEQUENCE: 19

Met Ser Ser Asp Leu Arg Leu Thr Leu Pro Glu Leu Val Arg Arg Leu
 1               5                  10                  15

Asn Gly Asn Gly Thr Ile Glu Ser Gly Arg Leu Pro Gly Gly Arg Arg
            20                  25                  30

Arg Ser Pro Asp Thr Thr Thr Gly Thr Ile Gly Val Thr Lys Thr Thr
        35                  40                  45

Glu Asp Pro Lys Glu Cys Ile Asp Pro Thr Gly Arg Pro Ala Pro
    50                  55                  60

<210> SEQ ID NO 20
<211> LENGTH: 61
<212> TYPE: PRT
<213> ORGANISM: Borna disease virus

<400> SEQUENCE: 20

Ser Asp Leu Arg Leu Thr Leu Leu Glu Leu Val Arg Arg Leu Asn Gly
 1               5                  10                  15

Asn Gly Thr Ile Glu Ser Gly Arg Leu Pro Gly Gly Arg Arg Arg Ser
            20                  25                  30

Pro Asp Thr Thr Thr Gly Thr Ile Gly Val Thr Lys Thr Thr Glu Asp
        35                  40                  45

Pro Lys Glu Cys Ile Asp Pro Thr Gly Arg Ser Ala Pro
    50                  55                  60
```